US010227403B2

(12) United States Patent
Imran et al.

(10) Patent No.: US 10,227,403 B2
(45) Date of Patent: Mar. 12, 2019

(54) PHARMACEUTICAL COMPOSITIONS AND METHODS FOR FABRICATION OF SOLID MASSES COMPRISING POLYPEPTIDES AND/OR PROTEINS

(71) Applicant: INCUBE LABS, LLC, San Jose, CA (US)

(72) Inventors: Mir Imran, Los Altos Hills, CA (US); Mercedes Morales, San Jose, CA (US); Radhika Korupolu, San Jose, CA (US); Elaine To, San Jose, CA (US); Joel Harris, Mountain View, CA (US); Mir Hashim, Fremont, CA (US)

(73) Assignee: InCube Labs, LLC, San Jose, CA (US)

( * ) Notice: Subject to any disclaimer, the term of this patent is extended or adjusted under 35 U.S.C. 154(b) by 0 days.

(21) Appl. No.: 15/144,733

(22) Filed: May 2, 2016

(65) Prior Publication Data
US 2017/0051051 A1  Feb. 23, 2017
US 2018/0208651 A9  Jul. 26, 2018

Related U.S. Application Data

(63) Continuation-in-part of application No. 14/714,136, filed on May 15, 2015, now Pat. No. 10,039,810, which is a continuation-in-part of application No. 14/714,126, filed on May 15, 2015, now Pat. No. 10,058,595, application No. 15/144,733, which is a continuation-in-part of application No. 14/714,146, filed on May 15, 2015, and a continuation-in-part of application No. 14/714,120, filed on May 15, 2015, now Pat. No. 10,098,931.

(60) Provisional application No. 62/156,105, filed on May 1, 2015, provisional application No. 61/993,907, filed on May 15, 2014, provisional application No. 62/159,134, filed on May 8, 2015.

(51) Int. Cl.
| | |
|---|---|
| *A61K 38/28* | (2006.01) |
| *A61K 9/00* | (2006.01) |
| *A61K 9/14* | (2006.01) |
| *A61K 9/16* | (2006.01) |
| *A61K 9/20* | (2006.01) |
| *C07K 16/00* | (2006.01) |
| *C07K 16/24* | (2006.01) |

(52) U.S. Cl.
CPC .......... *C07K 16/241* (2013.01); *A61K 9/0065* (2013.01); *A61K 9/145* (2013.01); *A61K 9/146* (2013.01); *A61K 9/1623* (2013.01); *A61K 9/1635* (2013.01); *A61K 9/1641* (2013.01); *A61K 9/2018* (2013.01); *A61K 9/2027* (2013.01); *A61K 9/2031* (2013.01); *A61K 38/28* (2013.01); *C07K 16/00* (2013.01); *C07K 16/244* (2013.01); *C07K 2317/21* (2013.01); *C07K 2317/24* (2013.01); *C07K 2317/40* (2013.01); *C07K 2317/76* (2013.01)

(58) Field of Classification Search
CPC .............. A61K 2300/00; A61K 9/2054; A61K 9/2866; A61K 9/2027; A61K 9/2018; A61K 9/2031; A61K 9/205; A61K 9/0065; A61K 9/1623; A61K 9/5042; A61K 9/146; C07K 16/244; C07K 16/00; C07K 16/241
See application file for complete search history.

(56) References Cited

U.S. PATENT DOCUMENTS

| | | | |
|---|---|---|---|
| 9,149,617 B2 | 10/2015 | Imran | |
| 10,058,595 B2 | 8/2018 | Morales et al. | |
| 2012/0003306 A1 | 1/2012 | Sung et al. | |
| 2013/0165372 A1 | 6/2013 | Imran | |
| 2013/0165859 A1* | 6/2013 | Imran | A61M 31/002 604/101.01 |
| 2015/0328287 A1 | 11/2015 | Morales et al. | |
| 2015/0329630 A1 | 11/2015 | Morales et al. | |

(Continued)

FOREIGN PATENT DOCUMENTS

WO   WO-2007021101 A1   2/2007

OTHER PUBLICATIONS

Berger, et al. Structure and interactions in covalently and ionically crosslinked chitosan hydrogels for biomedical applications. European Journal of Pharmaceutics and Biopharmaceutics 57.1 (2004): 19-34.

Corti, et al. Sustained-release matrix tablets of metformin hydrochloride in combination with triacetyl-β-cyclodextrin. European Journal of pharmaceutics and biopharmaceutics 68.2 (2008): 303-309.

(Continued)

*Primary Examiner* — Robert S Landsman
*Assistant Examiner* — Bruce D. Hissong
(74) *Attorney, Agent, or Firm* — Wilson Sonsini Goodrich And Rosati, P.C.; Joel M. Harris

(57) ABSTRACT

Embodiments of the invention provide shaped masses (SM) comprising one or more drugs such as proteins or polypeptides and methods for forming and delivering such SM's. One embodiment provides a SM comprising a drug e.g., a protein or polypeptide having a biological activity in the body of a mammal. The SM is formed by compression of a precursor material (PM) comprising the drug wherein an amount of biologically active drug in the SM is a minimum level to that in the PM. Drugs which may be incorporated into the SM include insulin, incretins and immunoglobulins e.g., interleukin neutralizing antibodies or TNF-α-inhibiting antibodies. Embodiments of the invention are particularly useful for the oral delivery of drugs which would be degraded within the GI tract, wherein the SM containing the drug is formed as or incorporated into a tissue penetrating member which is inserted into the intestinal wall after oral ingestion.

52 Claims, 10 Drawing Sheets

(56) References Cited

U.S. PATENT DOCUMENTS

2015/0329631 A1 11/2015 Morales et al.
2015/0329633 A1 11/2015 Morales et al.

OTHER PUBLICATIONS

Genovese, et al. A Phase II Randomized Study of Subcutaneous Ixekizumab, an Anti-Interleukin-17 Monoclonal Antibody, in Rheumatoid Arthritis Patients Who Were Naive to Biologic Agents or Had an Inadequate Response to Tumor Necrosis Factor Inhibitors. Arthritis & Rheumatology 66.7 (2014): 1693-1704.
Hueber, et al. Effects of AIN457, a fully human antibody to interleukin-17A, on psoriasis, rheumatoid arthritis, and uveitis. Sci Transl Med. Oct. 6, 2010;2(52):52ra72. doi: 10.1126/scitranslmed.3001107.
Ilango, et al. Dissolution studies on tablets of ibuprofen using chitosan. Indian journal of experimental biology 37 (1999): 505-508.
Mease, et al. Brodalumab, an anti-IL17RA monoclonal antibody, in psoriatic arthritis. New England Journal of Medicine 370.24 (2014): 2295-2306.
Mirsky, et al. The destruction of I131-labeled insulin by rat liver extracts. Journal of Biological Chemistry 214.1 (1955): 397-408.
Zhou, et al. Cyclodextrin functionalized polymers as drug delivery systems. Polym. Chem., 2010,1, 1552-1559.

* cited by examiner

α-Cyclodextrin

β-Cyclodextrin

γ-Cyclodextrin

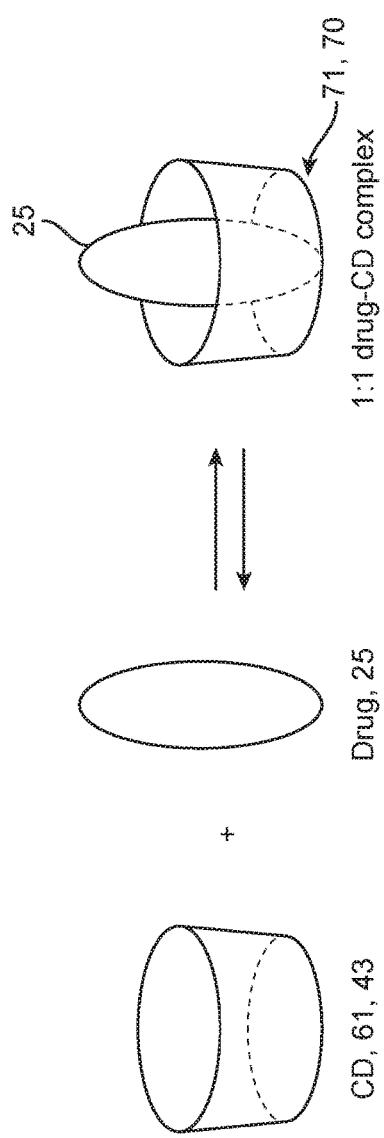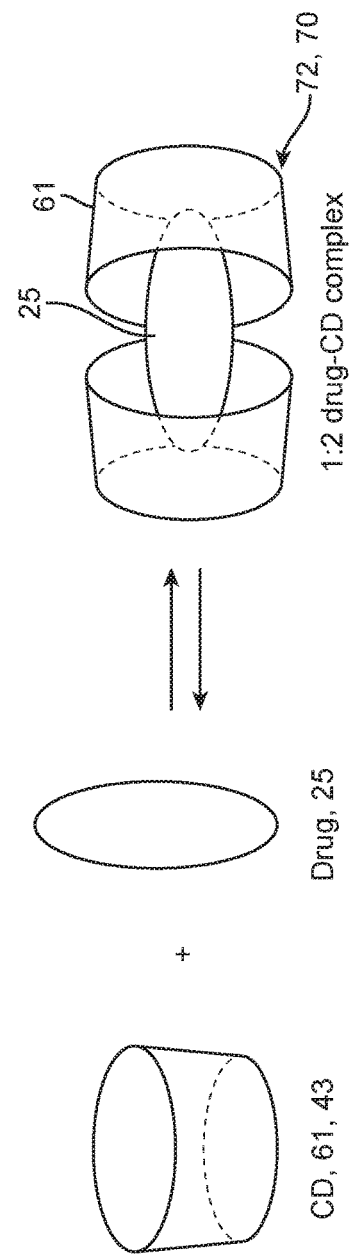

PHARMACEUTICAL COMPOSITIONS AND METHODS FOR FABRICATION OF SOLID MASSES COMPRISING POLYPEPTIDES AND/OR PROTEINS

CROSS-REFERENCE TO RELATED APPLICATIONS

This application claims the benefit of priority to U.S. Provisional No. 62/156,105, filed May 1, 2015, the entire content of which is incorporated herein by reference in its entirety; this Application is also a continuation-in-part of the following U.S. patent application Ser. Nos. 14/714,120, 14/714,126, 14/714,136, and 14/714,146, all filed on May 15, 2015, which are incorporated hereby by reference in their entirety.

This application is also related to U.S. application Ser. No. 13/532,589, now U.S. Pat. No. 9,149,617, entitled "Device, System And Methods For The Oral Delivery Of Therapeutic Compounds" filed Jun. 25, 2012, which is incorporated by reference herein for all purposes.

FIELD OF THE INVENTION

Embodiments described herein relate to pharmaceutical compositions and methods of fabrication of pharmaceutical compositions comprising solid masses comprising proteins and polypeptides. More specifically, embodiments described herein relate to pharmaceutical compositions and methods of production of pharmaceutical compositions comprising solid shaped masses comprising proteins and/or polypeptides having a biological activity wherein at least a portion of the biological activity of the protein or polypeptide is maintained after formation of the solid mass.

BACKGROUND OF THE INVENTION

While there has been an increasing development of new drugs for the treatment of a variety of diseases, many including proteins, antibodies and peptides have limited application because they cannot be given readily formed into solid shapes for oral or other form of delivery and/or encapsulated. One challenge in this area is that the process of fabrication of a drug comprising a protein, peptide or antibody into tablet or other solid form can result in loss in the bioactivity of the drug due to disruption of the structure of the protein from the fabrication process. This is due to the fact that many proteins have complex internal structures that define their biological activity. Disruption in the structure of a protein and/or polypeptide can result in its deactivation or considerable decline of its bioactivity. Such disruption can result from fabrication processes such as molding, compression, milling, grinding or encapsulation or other related process. What is needed is a method for forming bioactive compounds such as proteins, antibodies and peptides into solid or semisolid shapes for oral or other form of delivery to a human or other mammal without significant loss of bioactivity of the compound.

BRIEF SUMMARY OF THE INVENTION

Various embodiments of the invention provide pharmaceutical compositions comprising solid shaped masses including one or more drugs and methods of production of the shaped masses. The drug (also referred to herein as API or active pharmaceutical ingredient) may comprise one or more polypeptides or proteins such as various antibodies and other immunoglobulins which have a biological activity in the body of a human or other mammal which is degraded by secretions in the GI tract such as those from/in the stomach, pancreas and the small intestine including various proteases and other proeteolytic enzymes in the small intestine. Many embodiments provide methods for forming solid shaped masses comprising one or more proteins or polypeptides where the shaped masses are formed by the shaping of a precursor material and wherein at least a portion of the biological activity of the protein or polypeptide in the shaped mass is substantially preserved after formation relative to the biological activity of the protein, polypeptide or other therapeutic agent prior to formation. In many embodiments, the shaping is done by compression of the precursor material where the compressive forces are selected to minimize degradation of the biological activity of the protein or polypeptide. Other shaping methods are also contemplated wherein, the degradations of the biological activity of the precursor material is minimized. Typically, the precursor material will comprise a powder mixture comprising the drug and one or more excipients. The precursor material may also comprise a liquid, slurry or paste. The excipients may include one more of a lubricant, a binder, bulking agent, etc. In particular embodiments, the excipients can include a drug sequestering polymer such as a water swellable polymer e.g., a hydrogel which is formulated with the shaped mass in a dry form and then swell once delivered to the target tissue site such as the wall of the small intestine. Once swollen, the hydrogel forms a three dimensional structure which acts as a drug depot or barrier structure to contain and control the release of the protein or polypeptide or other drug from the shaped mass. The barrier structure is subsequently biodegraded (e.g., by hydrolysis) within the intestinal wall (or other location). Embodiments of the invention are particular useful for the oral delivery of such therapeutic agents (e.g., polypeptides, and proteins including antibodies (e.g., tnf-α inhibiting antibodies) having a biological activity which is degraded by secretions of the GI tract including secretions from the stomach, pancreas and small intestine. Further, embodiments are also particularly useful for controlling the rate of release into tissue/and or into the blood stream of such therapeutic agents once they are placed in the wall of the small intestine (or other location in the GI tract or other tissue site in the body) through the use of one or more embodiments of drug sequestering polymers described herein.

In various embodiments, the drug sequestering polymer may also comprise a polymer which non-covalently and reversibly interacts with the drug so as to slow a release rate of the drug from the shaped mass into tissue surrounding the shaped mass such as intestinal and/or peritoneal wall tissue once the shaped mass is placed there. Such reversible non-covalent interactions can comprise one or more of electrostatic Coulomb, dipole-dipole, van der Waals, solvophobic, hydrophobic, or hydrogen bonding interactions or other supramolecular chemical interactions. In many embodiments such drug sequestering polymers can include compounds having a cavity typically a hydrophobic cavity which reversibly interacts with the drug in the presence of aqueous tissue fluids (e.g., various interstitial fluids) surrounding the shaped mass to form a reversible inclusion complex comprising the drug and the drug sequestering polymer. The complex also known as an inclusion compound can be configured to be reversible based in part on a change in the chemical, fluidic or other physical property in the fluid dissolving or otherwise surrounding the host-guest complex. Such changes in the physical properties can include, for example, a change in the pH of the fluid (e.g. an increase in pH from about 7 to a neutral pH) and or a change in the concentration of the inclusion compound (e.g., a decrease in the concentration as inclusion compound diffuses down gradient and/or more dilute aqueous tissue fluids are drawn to the host guest complex by osmolar gradient, hydrophilic or other related forces). In these and related embodiments, the drug sequestering polymer may comprise cyclic oligosaccharides, including various cyclodextrins comprising 5 or more α-D-glucopyranoside units. Typically, cyclodextrins have a toroid shape with a hydrophoic cavity and larger and smaller openings encircled by what are known as the primary and secondary faces respectively (which consist of what are known as the primary and secondary groups of exposed hydroxyl groups. The hydrophobic cavity is what interacts with drug to form the inclusions compound (by one or more super-molecular interactions, e.g., hydrophobic, hydrogen bonding interactions, etc.) and its size (e.g., the primary or secondary opening size) can selected to complex with specific drugs or other therapeutic agents. Example cyclodextrins may include one or more of a cyclodextrin: (alfa) a 6-membered sugar ring molecule; β (beta)-cyclodextrin: a 7-membered sugar ring molecule; or γ (gamma)-cyclodextrin: 8-membered sugar ring molecule. In preferred embodiments the cyclodextrin comprises the β (beta)-cyclodextrin form as the cavity of this particular cyclodextrin has size for accommodating a variety of drugs and other therapeutic agents such as various hormones and vitamins. The reversible interactions between the cyclodextrin or other drug sequestering polymer can be selected to slow or otherwise control the release of the drug into the tissue surrounding the shaped mass relative to the release rate of the drug were the drug sequestering polymer not there. In various embodiments, the ratio the drug sequestering polymer to drug can be selected to decrease the release rate of the drug by selectable amounts (e.g., by 50, 100, 150, 200, 250, 500% etc.). In various embodiments, the ratio of drug sequestering polymer to drug can be in the range of 4:1 to 1:4 with narrower range of 2:1 to 1:2 and specific embodiments of 2:1, 3:2, 1:1, 2:3 and 1:2. The ratio can also be selected such that two or more drug sequestering polymer interact with each drug molecule (e.g., via a ratio of drug sequestering polymer to drug of 2:1). In additional or alternative embodiments the cyclodextrin molecule can be covalently copolymerized with one or more water soluble polymers such that the resulting copolymer contains multiple cyclodextrin groups which can each bind with a drug molecule. This allows for a single copolymer molecule containing the CD groups to bind to multiple drug molecules allowing for lower ratio of cyclodextrin containing drug sequestering molecule to drug molecule in the shaped mass.

The excipient may also comprise one or more salts which are selected to control the pH or otherwise interact with the protein, polypeptide or other drug or therapeutic agent to control the release of drug into the wall of the small intestine or other target delivery site. For some embodiments the salts may selected to reversibly slow the release of the drug, such as in the case of insulin, wherein it promotes the formation of insulin multimers, which aggregate in the fluid surrounding and the shaped mass and/or in a bioavailable form of insulin then subsequently disassociate in vivo into the more bioavailable insulin monomers when the pH increases due to the acid in the tissue fluid surrounding the shape mass becoming diluted and/or the insulin multimer diffusing or otherwise being transported away from the interface of the interface between the shaped mass and the tissue and/or tissue fluid (e.g. interstitial fluid) surrounding the shaped mass.

In various embodiments, the shaped mass may be in the form of a tablet, micro-tablet, pill or slug shape. Other shapes are also considered including spherical. In particular embodiments, the shaped mass can also be in the form of a bead or micro-bead which is inserted or otherwise formulated into embodiments of a tissue penetrating member described herein. Multiple such beads may formulated into the tissue penetrating member, with different beads formulated to have different drug release (e.g. by elution) profiles so as to achieve a bi-modal or other multi-modal release profile (e.g., tri-modal etc.). Multiple bead embodiments can also be configured so as to have beads comprising different drugs so as to deliver different drugs (e.g., a first and second antibody). In use, such embodiments allow for the simultaneous delivery of multiple drugs (e.g. such as those used to in a multidrug regimen to treat a particular condition or conditions) as well as achieve a varied release profile of drug e.g., to have a fast (e.g. minutes) and a slower (e.g. hours) release of drug.

According to one or more embodiments, the shaped masses produced using embodiments of the formation process can have another property such as density or particle grain size (of the powder used to formulate the shaped mass) which is correlated to minimum level of bioactivity of the protein or peptide. Also, that correlated property may be consistently maintained within a selected range within a given lot of shaped masses as well from lot to lot. Embodiments of the solid masses described herein can be configured to be used in combination with any suitable drug delivery system to be administered via any appropriate route of administration for the condition to be treated. Such routes of administration can include without limitation, oral, sublingual parenteral, intravenous, intramuscular, intra-ventricular, intra-cardiac, For example, according to one embodiment, insulin containing micro-tablets (basal, fast-acting insulin or a combination of both) can be taken orally and delivered into the small intestine where the drug is delivered into the wall of the small intestine where the tablet(s) dissolves to release the drug into the blood stream. In another embodiment, insulin containing micro tablets can be injected or otherwise placed subcutaneously (e.g. intramuscularly) where they dissolve to release insulin into the bloodstream.

In one aspect, the invention provides pharmaceutical compositions comprising solid shaped masses comprising a drug or other therapeutic agent having a biological activity in the body of a mammal which is degraded by secretions of the GI tract. The shaped mass is configured to release the drug into wall tissue of the GI tract such as wall tissue of when the mass is positioned in or adjacent such tissue such that the biological activity of the drug is substantially preserved. Also, preferably the biological activity of drugs after formation from a precursor material such as a powder is preserved above a minimum threshold level (e.g., above 70%). The biological activity may be correlated to the structural integrity of the drug post formation (e.g. by correlating bioactivity assays to chemical assays), such that on, a compositional level, a selected percentage of the drug (e.g., on a weight basis) is maintained post formation relative to that in the precursor material. Typically, the shape will be formed by a compression process (e.g. compression molding), though other processes are also contemplated such as non-compressive molding. The drug may comprise a protein, peptide or antibody wherein the biological activity of the drug in the shaped mass is at least 70% to that prior to compression and more preferably, at least 90% to that prior to compression and still more preferably at least 95%. These numbers may also correspond to a weight percentage of biologically active drug remaining in the shaped mass relative to that in the precursor material (e.g., by correlating biological activity assays to chemical assays for weight composition as described above). In these and related embodiments, the shaped mass can have a density in a range of about 1.00 and 1.15 mg/mm3 and in more preferred embodiments, 1.02 and 1.06 mg/mm3. The shape will typically comprise a pellet shape but may also have a tablet, conical, cylindrical, cube, sphere or other like shape.

In another aspect, the invention provides therapeutic compositions in form of a shaped mass comprising a drug or other therapeutic agent and a drug sequestering polymer Thy drug may comprise a protein or polypeptide which has a biological activity in the body of a mammal which is degraded in the presence of secretions of the GI tract such as those in the stomach and small intestine including various proteolytic enzymes found in the small intestine. The shaped mass is configured to release the drug into wall tissue of the GI tract such as wall tissue of the small intestine when the mass is positioned in or adjacent such tissue such that the biological activity of the drug is substantially preserved. The drug sequestering polymer interacts with fluids in wall tissue of the GI tract to function as an in situ barrier structure to slow or otherwise control the release of the drug from the shaped mass into said tissue. According to one or more embodiments, the drug sequestering polymer comprises a water swellable polymer such as hydrogel which swells in the presence of fluids in the wall tissue of the GI tract to form the in situ barrier structure. The swollen hydrogel may be configured then degraded by at the tissue site to release the drug and/or increase the release rate. Other drug sequestering polymers are also considered such as various lactic acid polymers and cyclodextrins. The drug sequestering polymer (ds-polymer) may slow the release of drug a selected amount for example in a range of about 50 to 250% as compared to a rate when the ds polymer is not present. This can be achieved by selection of one or more of the structure of the ds-polymer and/or the amount or ratio of ds-polymer to drug. In particular embodiments, the ratio of ds-polymer to drug can be in a range of 4:1 to 1:4 and more preferably in a range of 2:1 to 1:2 with a particular embodiment of 1:1. In preferred embodiments an amount of biologically active drug in the shaped mass is at least about 70% by weight to that in the precursor material and more preferably at least about 80% and still more preferably at least 95%. The precursor material may have one or properties to facilitate such preservation of biological activity post formation including for example a particle size in the range of 50 to 450 μm. The density of the shaped mass may in various embodiments may be in a range of about 0.8 to about 1.10 mg/mm3.

Related embodiments provide methods of delivering a drug or other therapeutic agent using above embodiments of the shaped mass to patients in need thereof. One such embodiment comprises inserting into the intestinal wall of the patient a shaped mass comprising the drug and a water swellable polymer such as a hydrogel. As described above, the drug has a biological activity in the body of a human which is degraded in the presence of secretions of the GI tract and the shaped mass is configured to release the drug into wall tissue of the GI tract when the shaped mass is positioned in or adjacent the intestinal wall tissue such that the biological activity of the drug is substantially preserved. The water swellable polymer is then swollen in the presence of fluids in the intestinal wall or adjacent tissue to form a barrier structure which sequesters the drug within the barrier structure so as to slow a release rate of the drug from the shaped mass into intestinal wall or adjacent tissue such as the peritoneal wall. The reduction in the release rate of the drug achieved by the water swellable polymer can be in the range of 50 to 250% or more. After a selected period of time (e.g., 4 hours to seven days in some cases) the water swellable polymer is degraded by in vivo chemical reactions (e.g., hydrolysis) such that the integrity of the barrier structure is compromised and the drug is released and/or release rate is increased to that rate without the barrier structure. In many embodiments, the shaped mass comprising the drug is contained or otherwise incorporated into a tissue penetrating member (e.g., a degradable needle, dart or shape having a pointed tissue penetrating tip) which is inserted and penetrates into the patients intestinal wall (or other GI wall tissue site) using one or more embodiment of a swallowable drug delivery device described in U.S. Pat. No. 9,149,617. Embodiments of the aforementioned methods are particularly useful for orally delivering drugs to a patient which otherwise have to be injected due to fact that they are broken down by secretions in the GI tract including those of the stomach, small intestine and pancreas. They are also particularly useful for controlling the release of drug once it so positioned in the wall of the small intestine or adjacent tissue so as to produce an extended release of the drug over a period of hours or days.

In another aspect, the invention provides therapeutic compositions in form of a shaped mass comprising a drug or other therapeutic agent and a drug sequestering polymer. Thy drug may comprise a protein or polypeptide which has a biological activity in the body of a mammal which is degraded in the presence of secretions of the GI tract such as those in the stomach and small intestine including various proteolytic enzymes found in the small intestine. The shaped mass is configured to release the drug into wall tissue of the GI tract such as wall tissue of small intestine or the peritoneal wall when the mass is positioned in or adjacent such tissue such that the biological activity of the drug is substantially preserved. The drug sequestering polymer non-covalently interacts with the therapeutic agent in the presence of fluids (e.g., interstitial fluid, secretions etc.) in the tissue at the tissue site so as to decrease a release rate of therapeutic agent into the tissue at the tissue site as compared to a release rate of the therapeutic agent without the drug sequestering polymer present. The non-covalent interactions may comprise one or more of acid, hydrogen bonding, electrostatic, hydrophobic or solvophobic interactions. In many embodiments, the drug sequestering polymer has a hydrophobic cavity which interacts with drugs in the presents of fluids in a wall of the GI tract (such as that in the wall of the small intestine or peritoneal wall) so as to reversibly form an inclusion complex or compound which serves to decrease the release rate of the drug into tissue in the GI wall and/or the vasculature thereof. The complex may be formed based on at least one of acid, hydrophobic, hydrogen bonding or solvophobic interactions. Further the inclusion complex may be released so as to release the drug by based on a change in one or more of the pH or dilution of the complex in the tissue fluid adjacent the shaped mass. Typically, this involves an increase in the pH (going from acidic to neutral) and/or the complex becoming more dilute (e.g., a decreased concentration) in the surrounding fluid. The drug may either be singly or doubly complexed, the latter case being where the drug by is complexed by two molecules of the ds-molecule having the hydrophobic cavity at two separate locations on the drug molecule. The degree of complexing can be selected based on the particular ds-molecule selected (e.g., its structure), the particular drug, the inclusion in the shaped mass of excipients such as various acids to promote inclusion complex/compound formation, those that promote its reversal (e.g., various bases) and the ratio of the ds-molecule to the drug (e.g., a ration equal to or greater than 2:1). In these and related embodiments the ds-molecule can be selected so as to slow the release rate of the drug from 20 to 400% with narrow range embodiments of 30 to 300%, 50 to 250%, 50 to 200%, 50 to 150% and 50 to 100%. This can be achieved both by the selection of the particular ds-molecule (e.g., beta-cylcodextrin) and its ratio to the drug. In various embodiments, that ratio can be in a range of 1:4 to 4:1 with narrow ranges of 2:3 to 3:2 and 1:2 to 2:1. In specific embodiments the ratio of ds-molecule to drug can be 2:1. In various embodiments, the drug may comprise a glucose regulating compound such as insulin or incretin; a hormone such as parathyroid hormone or growth hormone; or antibody such as a tnf-α antibody or an interleukin neutralizing antibody examples of which are described herein.

Related embodiments provide methods of delivering a drug or other therapeutic agent using above embodiments of the shaped mass to patients in need thereof. One such embodiment comprises inserting into the intestinal wall of the patient a shaped mass comprising the drug and a ds-polymer configured to non-covalently interact with the drug in the presence of fluids in the intestinal wall, typically to form an inclusion complex with the drug. As described above, the drug has a biological activity in the body of a human which is degraded in the presence of secretions of the GI tract and the shaped mass is configured to release the drug into wall tissue of the GI tract when the shaped mass is positioned in or adjacent the intestinal wall tissue such that the biological activity of the drug is substantially preserved. After insertion into the wall, the shaped mass becomes wetted by the aqueous tissue fluids of the GI wall and the ds-polymer non-covalently interact with the drug in the presence of the GI wall tissue aqueous fluids so as to slow the rate of release of the drug from the shaped mass for example by amounts in the range of 50 to 250% or more. Typically this is achieved by the ds-polymer forming an inclusion complex with the drug. In many embodiments the ds-molecule for performing this function comprises one that has a hydrophobic cavity which hydrophobically or otherwise non-covalently interacts with the drug to form the inclusion complex. After being so complexed, after a period of time, physical and/or chemical changes in the local fluidic environment surrounding the inclusion complex cause the drug to disassociate from the ds-molecule These change may correspond to one or more of changes in the pH or concentration of the inclusion complex in its local fluidic environment (e.g. the fluidic environment surrounding the inserted shaped mass). Typically, the ds-molecule having such a hydrophobic cavity will correspond to a cyclic oligosaccha-rides which preferably correspond to various cyclodextrin molecules known in the art such as alfa, gamma and beta forms of the molecule, though other forms are also considered. In a preferred embodiment, the ds-molecule corresponds to a beta-cyclodextrin molecule the structure of which is known in the art and described herein. Embodiments of the shaped mass comprising the drug are typically contained or otherwise incorporated into a tissue penetrating member (e.g., a degradable needle, dart or shape having a pointed tissue penetrating tip) which is inserted and penetrates into the patients intestinal wall (or other GI wall tissue site) using one or more embodiment of a swallowable drug delivery device described in U.S. Pat. No. 9,149,617. Embodiments of the aforementioned method are particularly useful for orally delivering drugs to a patient which otherwise have to be injected due to fact that they are broken down by secretions in the GI tract including those of the stomach, small intestine and pancreas. They are also particularly useful for controlling the release of drug once it so positioned in the wall of the small intestine or adjacent tissue so as to produce an extended release of the drug over a period of hours or days.

In various embodiments where the drug sequestering polymer (ds-polymer) has a hydrophobic cavity to complex the drug so as to form an inclusion complex (inclusion compound) the ds-polymer may correspond to a cyclic oligosaccharide such as various cyclodextrins. In preferred embodiments the cyclodextrin comprises beta cyclo-dextrin (having a seven membered sugar ring), however cyclodextrins are also considered including alfa and gamma-cyclo-dextrins (having six and 8 membered sugar rings respectively). Further, in additional or alternative embodiments the cyclodextrin molecule can be copolymerized with a long chain organic molecule such that the copolymer has multiple cyclodextrin inclusion sites on a single copolymer molecule allowing for the formation of multiple inclusion complexes on a single such copolymer. In use such copolymerized molecules allow for one or more of: i) a greater degree of complexing with a smaller quantity of the ds-molecule; ii) greater control over the release rate of the drug (due to increased complexing); and iii) a further reduction in the release rate of the drug and thus an increase in the release period.

According to various embodiments, in addition to the drug and other excipients, the shaped mass can be formed from a biodegradable material that is configured to dissolve or otherwise degrade in the wall of the intestine or adjacent tissue such as the small intestine and/or peritoneal wall (or another tissue site, e.g., an intramuscular site) so as to release the drug into the intestinal wall where it diffuses or otherwise is transported into the capillary bed of the intestinal wall and then is carried by the circulatory system throughout the body. The shaped mass may be inserted or otherwise incorporated into a structure, such as a tissue penetrating member that is made from such a biodegradable material. The tissue penetrating member being configured to be penetrate and be inserted into the wall of the small intestine (or other lumen in the GI tract) by the application of force on the tissue penetrating member. Suitable biodegradable materials include various sugars such as maltose, mannitol, cyclodextrins and sucrose; various lactic acid polymers such as polyglycolic acid (PGA), polylactic acid (PLA); polyglycolic lactic acid (PGLA); various polyethylenes including polyethylene oxides, various celluloses, such as HPMC (hydroxypropyl methyl cellulose), PVOH (polyvinyl alcohol), silicone rubber and other biodegradable polymers known in the art. The material and other properties of the degradable polymer and shaped mass can be selected to produce selectable rates of degradation in the intestinal wall. According to one or more embodiments the rates of degradation can be selected to achieve various pharmacokinetic parameters such as $t_{max}$, $C_{max}$, $t_{1/2}$, etc. In one more specific embodiments, the materials properties of the shaped mass can be selected so as to have the shaped mass degrade within the intestinal wall to achieve a $C_{max}$ for the selected drug(s) in a shorter time period than a time period to achieve a $C_{max}$ for an extravascularly injected dose of the drug.

In one embodiment, the drug in the shaped mass comprises insulin or an analogue for the treatment of diabetes or other glucose regulation disorder. The insulin may be obtained from any suitable source (e.g. human insulin and/or that generated using recombinant DNA methods) and may correspond to basal or fast acting insulin or a combination of both. In another application, the drug comprises an incretin such as exenatide for the treatment of a glucose regulation disorder. In these and related embodiments the compression or other molding process is configured to preserve the biological activity of the insulin or incretin so as to be able to allow the drug to treat diabetes or other glucose regulation disorder once released into the body of a patient.

Still other embodiments provide methods of preparing a shaped mass comprising a drug wherein the drug comprises an antibody such as IgG or an antibody from the TNF inhibiting class of antibodies such as adalimumab (Humira®), infliximab (Remicade®), certolizumab, pegol (Cimzia®), golimumab (Simponi®), or etanercept (Enbrel®).

Still other embodiments provide methods of preparing a shaped mass comprising a drug wherein the drug comprises an antibody, immunoglobulin or other protein that neutralizes the biological/biochemical effects of interleukins including interleukins 1 through interleukin 36 wherein the biological activity (e.g., its binding affinity to a selected antigen and/or neutralizing ability of the selected antigen) of the anti-body is preserved after formation of the shaped mass in amounts of 70, 80, 90 or 95% relative to that of a precursor material prior to formation such embodiments considered to comprise substantial preservation of the biological activity of the antibody or other therapeutic agent described herein. In such embodiments, the antibody or other neutralizing agent can be configured to neutralize the biological/biochemical effects of the particular interleukin by being configured to bind to the interleukin itself or the receptor for the interleukin preventing the receptor from being activated. Many embodiments provide shaped masses comprising antibodies which neutralize the biological effects of the interleukin 17 family of interleukins with particular embodiments comprising one or more of the antibodies Secukinumab, Brodalumab, and Ixekizumab. For example, according to one embodiment, the shaped mass can include a therapeutically effective dose of Secukinumab for the treatment of plaque psoriasis. In another embodiment, the shaped mass can include a therapeutically effective dose of Brodalumab for the treatment of psoriatic arthritis. In yet another embodiment the shaped mass can include a therapeutically effective dose of Ixekizumab for the treatment of psoriatic arthritis.

Still other embodiments provide methods of preparing a shaped mass comprising a drug wherein an outer coating or layer is formed over the drug using 3-D printing methods so as to produce a selectively shaped mass. Use of 3-D printing methods allow the shaped mass to be formed without the application of pressure and/or force on the mass. In use, such methods improve the yield of the drug in the final shaped mass due to decreased protein denaturation and/or other degradative effects on the drug. This in turn improves the bioactivity of the drug in the final shaped mass. Use of 3-printing also allows a variety of shapes to be produced without use of a mold or other related device reducing the potential for contamination and improving sterility. Such shapes may include for example, an arrow head shape, rectangle, pyramidal, spherical, hemispherical, conical and others. 3 D printing methods also allow for rapid customization of the drug mass shape and size for individual patient parameters, for example one or more of a patient's weight, medical condition and particular medical regimen (e.g. taking of medication once day, twice etc.). In still other embodiments, 3-D printing methods can be used to produce shaped masses configured to have a bimodal form of delivery, e.g. fast release and slow release.

Other embodiments provide an inventory comprising a plurality of shaped masses of a pharmaceutical composition comprising a drug such as a peptide, protein or immunoglobulin, wherein a property of the shaped composition, such as the biological activity of the drug after formation and/or density of the shaped mass, is maintained within a selected range for substantially the entire inventory. In use, such embodiments provide for the ability to maintain a uniform dosage and various pharmacokinetic parameters for one or more selected drugs delivered using embodiments of the shaped masses described herein.

Further details of these and other embodiments and aspects of the invention are described more fully below with reference to the accompanying figures.

BRIEF DESCRIPTION OF THE DRAWINGS

FIG. 1b is a perspective view of the embodiment of FIG. 1a.

FIG. 16a depicts the drug and cyclodextrin molecule prior to complex formation, FIG. 16b shows the drug sitting in the cyclodextrin cavity complexed with the cyclodextrin and FIG. 16c shows the drug released or decomplexed from the cyclodextrin.

FIG. 17a-17b are schematic views showing formation of a inclusion complex wherein the drug is singly (FIG. 17a) or doubly complexed (FIG. 17b) with a cyclodextrin molecule.

DETAILED DESCRIPTION OF THE INVENTION

Figure 3:
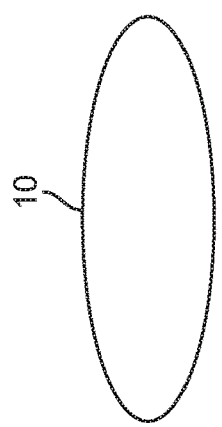
FIG. 3 is a lateral view showing an embodiment of the shaped mass having a hotdog/capsule like shape.
Figure 4:
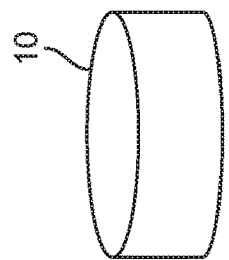
FIG. 4 is a lateral view showing an embodiment of the shaped mass having a tablet shape.
Figure 1C:
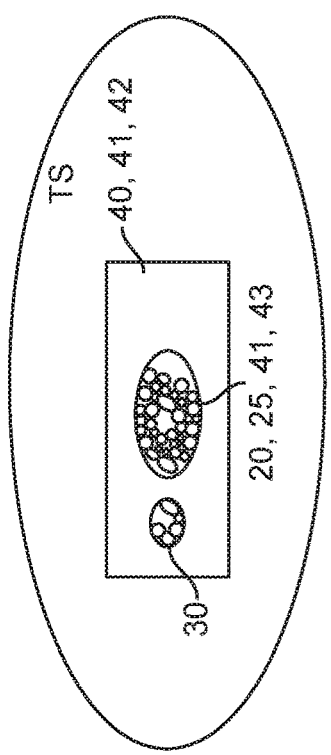
FIG. 1c is cross-sectional view showing an of the shaped mass including a drug sequestering polymer.
Figure 2:
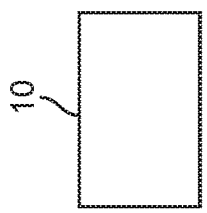
FIG. 2 is a lateral view showing an embodiment of the shaped mass having a cubical shape.
Figure 1A:
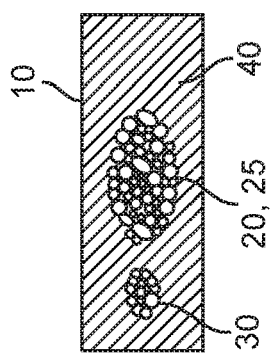
FIG. 1a is a lateral cross-sectional view showing an embodiment of the shaped mass having a cylindrical shape.
Figure 1B:
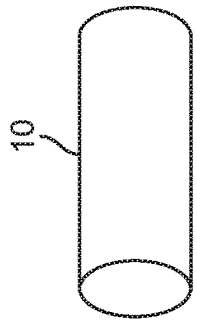
Figure 5:
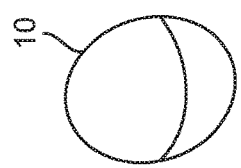
FIG. 5 is a perspective view showing an embodiment of the shaped mass having a spherical shape.
Figure 6:
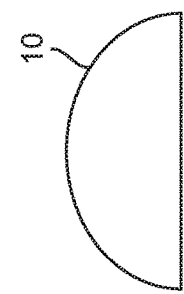
FIG. 6 is a lateral view showing an embodiment of the shaped mass having a hemispherical shape.
Figure 7:
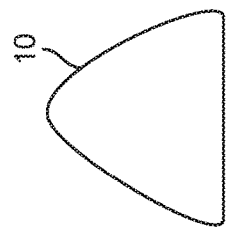
FIG. 7 is a lateral view showing an embodiment of the shaped mass having a pyramidal shape.
Figure 8:
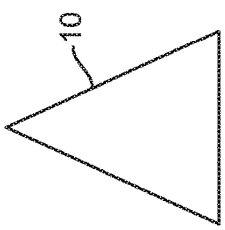
FIG. 8 is a lateral view showing an embodiment of the shaped mass having an arrow-head shape.
Figure 9:
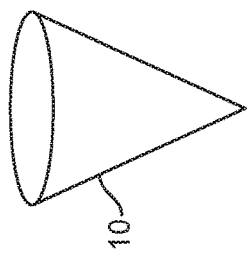
FIG. 9 is a perspective view showing an embodiment of the shaped mass having a conical shape.
Figure 10:
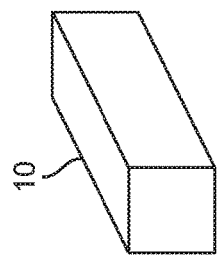
FIG. 10 is a perspective view showing an embodiment of the shaped mass having a rectangular shape.
Figure 11:
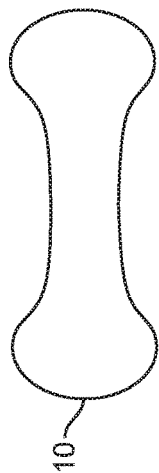
FIG. 11 is a perspective view showing an embodiment of the shaped mass having a dog boned shape.

With reference now to FIGS. 1-12, various embodiments of the invention provide pharmaceutical compositions in the form of solid shaped masses comprising one more drugs and methods for forming solid shaped masses comprising one or more drugs or other therapeutic agents. According to one or more embodiments, the drug may comprise one or more polypeptides and proteins such as various immunoglobulins proteins (e.g. an antibody) which have a biological activity (e.g. a binding affinity and/or neutralizing ability for an antigen, a glucose regulating ability, hormonal property, chemotherapeutic property, antiviral property and the like) which may be decreased by conventional solid pharmaceutical formulation processes (e.g., such as various compression processes used to form pills, tablets etc.) as such processes tend to degrade or otherwise damage the molecular structure of the protein or peptide. One embodiment of the shaped mass 10 is shown in FIGS. 1a and 1b comprises a therapeutic composition 20 which can include one or more drugs or other therapeutic agents 25; an excipient 30 and a material 40 which is incorporated with and or surrounds the drug. In some embodiments (e.g., that shown in FIG. 1b) material 40 may correspond to one which degrades within a target delivery site in the body (e.g., the wall of the small intestine) or otherwise interacts with tissue to release drug 25. Such materials may include which (polyethylene, various sugars, lactic acid polymer, PGLA and the like. In other embodiments, shown in FIG. 1c, material 40 may correspond to and/or include a drug sequestering polymer (ds-polymer) 41 described herein, which is configured to slow and otherwise control the release rate of drug 25 into the tissue site TS, (e.g., intestinal wall tissue in wall) where the shaped mass 10 is positioned. Ds-polymer 41 may also be incorporated into the therapeutic composition 20 along with drug 25 such that it can readily interact with the drug upon exposure to tissue fluids at the tissue site (e.g., interstitial fluid in the wall of the small intestine or peritoneal wall). Ds-polymer may correspond to various water swellable polymers such as various hydrogels, and also polymers such as various cyclodextrins. In embodiments where it comprises a water swellable polymer it can encase the drug so as to readily swell to form a barrier structure 50 as shown in FIGS. 12a and 12b.

According to many embodiments drug or other therapeutic 25 comprises a chemical compound which is degraded by secretions of the gastric tract (e.g., such as those in the stomach and small intestine) so as to loose its biological activity within the body of human or other mammal. Such drugs 25 may correspond to various polypeptides and proteins including, without limitations, various antibodies or other immunoglobulins such as tnf-α inhibiting antibodies or interleukin neutralizing antibodies; various glucose regulating compounds such as insulin and various incretins; various hormones such as thyroid hormone, parathyroid hormone, gonadotropin releasing hormone, growth hormone, testosterone, estrogen, pro-estrogen, luteinizing hormone, follicle stimulating hormone; and variants, derivatives and fragments thereof.

The shaped mass 10 can be formed from a variety of shaping processes known in the pharmaceutical arts. Typically, the shaped mass 10 will be formed by a compression process such as compression molding. The drug may comprise a protein, peptide or antibody. According to one or more embodiments, the biological activity of the protein or peptide in the mass is at least about 70% to that prior to compression, more preferably, at least 80% to that prior to compression, still more preferably about 90% to that prior to compression and still more preferably at least 95% prior to compression. (Note, as used herein, the term "about" refers a number within 10% of the stated value of the biological or other parameter (e.g., various pharmacokinetic parameters described herein)). These numbers may also correspond to a percentage (e.g. by weight) of the drug in the shaped mass relative to that prior to formation. In these and related embodiments, the shaped mass can have a density in a range of about 0.80 to about 1.15 mg/mm3, more preferably in a range from about 0.90 to about 1.10 mg/mm3, still more preferably in a range of about 1.02 to 1.06 mg/mm3 and still more preferably in a range from about 1.03 to 1.05 mg/mm3. The shape will typically comprise a pellet shape but may also have a tablet, conical, cylindrical, cube, sphere or other like shape. Also in these or alternative embodiments the particle size (e.g. diameter or widest dimension) of the powder used to make the shape mass may be in the range of 50 to 450 µm, more preferably between 100 to 400 µm and still more preferably between 200 to 400 µm.

According to various embodiments, the shaped mass 10 can be formed in part from a material that is configured to slow or otherwise control the release the drug into the intestinal wall and/or surrounding tissue (or other tissue site) after the shaped mass is inserted there (e.g., using various embodiments of a capsule or other swallowable/oral drug delivery devices such as those described in U.S. Pat. No. 9,149,617) with the effect in some embodiments being reversible. In various embodiments the slowed release and subsequent reversed slowed release of drug can occur by interactions of the material, and/or drug with the adjacent tissue. Such interactions can include one or more of dissolution, pH, hydrophilic hydrophobic or hydrogen bonding interactions. In preferred embodiments, the material is configured to dissolve or other otherwise degrade in tissue the wall of the intestine such as the small intestine (or another tissue site, e.g. an intramuscular site) so as to release the drug into the intestinal wall where it diffuses or otherwise is transported into the capillary bed of the intestinal wall and then is carried by the circulatory system throughout the body. As used herein, the term "degrade" includes one more of the processes of biodegradation, dissolving or disintegratation due to contact with a biological fluid (e.g., blood, interstitial fluid, lymph etc.) and/or tissue. Also the terms degrade(ation) can be used interchangeably. Suitable degradable materials include various sugars such as maltose, mannitol, cyclodextran and sucrose, various lactic acids polymers such as polyglycolic acid (PGA), polylactic acid (PLA); polyglycolic lactic acid (PGLA); various polyethylenes such as high density, low density and linear low density PE and PEO (polyethylene oxide), various cellulose polymers such as HPMC (hydroxypropyl methyl cellulose), CMC (carboxy methyl cellulose), MC (methyl cellulose), methacrylic acid-ethyl acrylate copolymer, methacrylic acid-methyl methacrylate copolymer PVOH (polyvinyl alcohol), silicone rubber. and other biodegradable polymers known in the art. The material and other properties of the degradable polymer and shaped mass can be selected to produce selectable rates of degradation in the intestinal wall. According to one or more embodiments, the rates of degradation can be selected to achieve various pharmacokinetic parameters such as $t_{max}$, $C_{max}$, $t^{1/2}$, etc. In one or more specific embodiments, the materials properties of the shaped mass (e.g., its chemical composition, solubility in interstitial fluids, size and shape) can be selected so as to have the shaped mass degrade within the intestinal wall to achieve a $C_{max}$ for the selected drug(s) in a shorter time period than a time period to achieve a $C_{max}$ for an extravascularly injected dose of the drug.

Embodiments of Methods for Fabricating Drug Containing Shaped Masses.

A description will now be provided of the fabrication process used to make various embodiments of the drug containing shaped masses described herein. The process includes a process for fabricating a powder containing one or more drugs and a shaped mass formation process for forming the powder into micro-tablets or other shaped masses comprising one or more drugs. For ease of discussion, the shaped masses will now be referred to as micro-tablets; however it should be appreciated that other forms and/or shaped for the shaped masses are equally applicable. It should also be appreciated that this process is exemplary and other processes are also considered.

Drug Powder Formation Process.

The process for formulation of a powder comprising the drug will now be described. Typically, it includes three steps. The first step is to prepare an aqueous solution of the drug and then add then add the desired excipients for the particular application. According to one more embodiments, the excipients can include a lubricant, a binder and a bulking agent. The lubricant is added to facilitate both micro-tablet formation and ejection from a mold. The lubricant may correspond to polyethylene glycol 3350 and in one or more embodiments may be added in proportion of approximately 10% w/w of the total batch mass. The bulking agent may correspond to mannitol and the binder may correspond to povidone. Other excipients which may be added include binders, fillers, disintegrates, stabilizers, buffers and antimicrobials. The proportions of the different ingredients, active and non-active, in the powder mixture are taken into consideration during the formulation process so as to achieve a desired therapeutic dose of the drug in the resulting micro-tablet.

The second step is to evaporate the aqueous mixture. The gently-mixed solution containing the drug and the excipients is then placed in a flexible and flat plate (for example, silicone plate) inside of a vacuum chamber containing desiccant. The chamber is then placed inside of a refrigerator or cold room and is connected to a vacuum line or pump. The solution is left under vacuum and low temperature, above 0° C., until it dries out completely.

The third step comprises milling the evaporated mixture to produce a fine powder. The evaporated mixture is placed in a low-protein-binding tube along with a single high-density milling ball, preferably, made of stainless steel or yttrium-stabilized zirconium. The milling is done using a rotator at max speed containing the tube film-wrapped to avoid moisture absorption or contamination. An ice pack is desirably placed on top of the tube to keep it cold. The room temperature can be controlled in a range for example from 60 to 64° F. The size of the milling tube, mass of the milling ball and duration of mixing may be selected to produce particular powder grain sizes, grain size homogeneity and powder density. For example, for the production of a 40 mg to 100 mg batch capacity, the use of a bottom-rounded 2 mL tube, a milling ball having a 0.44 g mass and a milling duration of 3 hours resulted in fine and consistent grain sizes, achieving more homogeneous and reliable density values.

Micro-Tablet Fabrication Process.

The process is desirably done in a clean and temperature-controlled room where the temperature is kept between 60-64° F. The micro-tablet formation is typically done via compression using a compression mold or other fixture to apply a compressive force to the powder including the drug. Two types of compression fixtures may be used, a semiautomatic one or a fully automatic version. For fabrication using the semiautomatic fixture, the micro-tablets are fabricated over a base which consists of two metal sheets connected to a force gauge stand by four cylinders, four springs and four vibration mounting stoppers. The top sheet has a cavity with a hole on it for a mold or well to slide in. The mold used for the compression has a 45 degree funnel ending in a well with required diameter and length to accommodate the powder for compression. A pin is attached to a pin holder and connected to the force gauge which can be moved up and down by a controlled motor operated by a 3-way switch.

The semiautomatic fabrication procedure can include the following steps: 1) positioning of a stopper, 2) placing a tablet mold on top of the stopper and a pin into the holder, 3) loading the powder required for the micro-tablet and letting it sink/settle into the mold hole, 4) compressing the powder into the mold by advancing a motorized pin (which is connected to force gauge) into the mold until a desired force is reach (i.e. compression force) and holding it in position with the applied force for a set time period (i.e. hold time), 6) removing the tablet metal stopper and place a dish to collect the tablet, and 7) lowering the pin with the motor switch until the micro-tablet exits the mold and collect the micro-tablet in a dish. The combination of compression force and hold time will determine the mechanical structure of the micro-tablet as well as the decrease in the bioactivity of the drug.

For the process using the automatic fixture, the processes of drug sinking, compression and ejection are fully automated. The mold rests in a base and is restrained by a mold holder by three screws. The mold bottom is in contact with a piece of metal referred to as a "gate" which can be move by the action of an air cylinder. The gate will stop the powder from falling down during loading and compression and will open during the ejection. An air cylinder is attached to the force gauge stand by a cylinder holder. This top air cylinder has a pin holder attached to its piston rod with a pin in it, which has the diameter required to be inserted into the mold hole and compress the powder. In general, a diameter of 0.0005" less than the diameter of the mold hole would be enough to have a tight fit between pin and mold hole. The top air cylinder connected to the pin extends to produce the powder compression and the ejection of the micro-tablet. A reed switch is connected to this cylinder to know the position of the piston rod. The stand also has a pneumatic vibrator with an air filter to vibrate the system and force the powder to move inside of the mold hole during loading. The three pneumatic components, gate air cylinder, compression/ejection top air cylinder and vibrator, are controlled by an electro-pneumatic system. This system consists of a power supply, programmable logic controller (PLC), four solenoids valves, reed switch, foot-switch pedal and a control panel that includes four regulators, four pressure gauges, micrographic panel and power switch.

In an automatic fashion, the controlling system is built and programmed in a way for the user to complete the following sequence: 1) user loads the powder; 2) user press pedal for initiation and hold it until the end of the sequence; 3) vibration starts (vibration duration and pressure can be modified at control panel); 4) powder is compressed by the pin due to the extension of the top cylinder (compression duration and pressure can be modified at control panel) followed by the retraction of the cylinder after compression; 5) gate is opened by the retraction gate air cylinder (gate pressure can be modified at control panel as well as the time for opening and closing the gate); 6) the micro-tablet is ejected by the new extension of top air cylinder (ejection duration and pressure can be modified at control panel) followed by the retraction of the cylinder after ejection; finally 7) the gate closes ending the sequence.

After the micro-tablet is fabricated, the length, weight, density and bioactivity of the drug in the pellet are measured. The bioactivity of the drug in the micro-tablet may be assayed using an Enzyme-linked immunosorbent assay (ELISA) or other immune assay known in the art. According to one or more embodiments, a separate compound, herein a bioactivity marker compound (herein bioactivity marker), may be included in at some batches, wherein the herein bioactivity marker has a molecular structure which has the same response (in terms of preservation of molecular structure and/or bioactivity) to compressive force used in the fabrication process as the drug included in the micro-pellet. The bioactivity marker however can be selected so that a bioactive amount of biomarker compound present in the micro-tablet and/or at any step in the fabrication process can be determined using a simple analytical test such as a colorometric and/or turbidity test.

Embodiments of Shaped Masses Comprising Insulin.

According to one or more embodiments of the pharmaceutical compositions described herein, the drug contained in the micro-tablet or other shaped mass comprises insulin or like molecule for the treatment of diabetes or other glucose regulation disorder. The insulin may be obtained from any suitable source e.g. human insulin and/or that generated using recombinant DNA methods known in the art. It may also correspond to basal or fast acting insulin (the type taken after eating a meal also known as meal time insulin) or a combination of both. Suitable basal insulins may include NP, Glargine and Detemir. Suitable fast-acting insulins may include aspart, glulisine, lispro, and regular. The specific dose of the insulin contained in the mass can be selected based on one more of the weight, age and/or other parameter of the patient. In specific embodiments, the micro-tablet may comprise between about 0.2 to about 0.8 mgrams of insulin. In various embodiments of the shaped mass comprising insulin, the shaped mass may also include one or more excipients comprising salts (e.g. sodium chloride, potassium chloride, etc.) and/or acids (e.g. citric acid) which are selected so as to control or adjust the drug or drug depot that is formed within the wall of intestine once the shaped mass is inserted into the wall of the small intestine or other delivery site. Such properties may correspond to the pH of the drug and/or drug depot. Control of the pH in turn can be used to control the elution/release profile of the insulin or other drug from the shaped mass (e.g. an incretin). For example in the case of insulin and its analogues, at low pH, insulin forms multimers (one example including a hexopolymer structure) which aggregate together and then disassociate in vivo (as the pH comes back to neutral levels) back to insulin monomers to release the insulin into its physiologically active form that acts on the body. Thus in one or more embodiments, acid salts such as citrates (e.g., citric acid) can be incorporated into the micro-tablet or other shaped mass along with insulin (or other like molecule) so as to slow the release rate of insulin into the interstitial fluids of the intestinal wall (or other target tissue site) and in turn into the blood stream.

The shaped mass may be formed according to one more methods described herein including compression forming methods/processes such as those described in the examples as well as 3D printing methods known in the art and also described herein. In these and related embodiments, the compression forming method is configured to preserve the biological activity of the insulin in the micro-tablet so as to be able to allow the drug to treat diabetes or other glucose regulation disorder once released into the body of a patient. The compression force use in such compression methods may be in the range of about of 0.5 to 4 pounds of force and more preferably in a range of about 1.5 to 3 about pounds of force. The weight percent of the insulin in the mass can range from about 10 to 95%, more preferably from about 20 to 95%, still more preferably from about 25 to 95% and still more preferably from about 80 to 95%. The biological activity and/or weight percentage of the insulin in the shaped mass may be in a range from about 88 to 99.8% to that prior to formation (e.g. from a powder used to form the micro-tablet). The density of the micro-tablet in such embodiments can range from about 0.95 to about 1.15 mg/mm$^3$, more preferably from about 1.0 to about 1.10 mg/mm$^3$. In preferred embodiments, the biological activity of the insulin in the shaped mass may comprise 99.2 to 99.8% of that prior to formation. The density of the micro-tablet in such embodiments can range from about 1.08 to 1.10 mg/mm$^3$. Measurement of the biological activity of the insulin in the shaped mass can be performed using assays known in the art, including ELISA or other immuno-assay methods.

According to one or more embodiments, the insulin containing shaped mass may also comprise one or more excipients including, for example, a lubricant, a bulking agent, a binding agent or binder and an acid salt as described herein. The lubricant is selected to reduce the amount of force required to eject drug containing shaped masses from a mold and may correspond to polyethylene glycol (PEG) an example including PEG 3350. The bulking agent may correspond to mannitol and the binder may correspond to povidone. The weight percent of the insulin in the mass can range from about 10 to 95%, more preferably from about 20 to 95%, still more preferably from about 25 to 95% and still more preferably from about 80 to 95%. The weight percent of PEG can range from about 1 to 10% with a specific embodiment of 5%. The weight percent of Mannitol can range from about 4 to 70% with a specific embodiment of 5%. The weight percent of Povidone can range from about 1 to 5% with a specific embodiment of 1%.

Embodiments of Shaped Masses Comprising Incretin.

According to one or more embodiments of the pharmaceutical compositions described herein, the drug contained in the micro-tablet or other shaped mass comprises an incretin such as exenatide for the treatment of a glucose regulation disorder such as diabetes. Other incretins are also contemplated. The shaped mass may be formed according to one more methods described herein including compression forming methods such as those described in the examples for insulin. As described above for insulin the compression forming method is configured to preserve the biological activity of the incretin in the micro-tablet so as to be able to allow the drug to treat diabetes or other glucose regulation disorder once released into the body of a patient. The specific dose of the exenatide or other incretin contained in the mass can be selected based on one more of the weight, age and other parameter of the patient. In specific embodiments, the micro-tablet may comprise between about 0.2 to about 1 to 5 mgms of exenatide. The density of the mass containing the incretin can be in the range of 1.04±0.10 mg Embodiments of Shaped Masses Comprising TNF Inhibiting Antibody.

According to one or more embodiments of the pharmaceutical compositions described herein, the drug contained in the micro-tablet or other shaped mass comprises an antibody from the TNF (Tumor Necrosis Factor) inhibitor class of antibodies (e.g., adalimumab) for the treatment of various autoimmune disorders (e.g. rheumatoid arthritis) which are characterized by the over production of tissue necrosis factor. In these and related embodiments, the compression and other aspects of the forming process used to fabricate the micro-tablet or other shaped mass is configured to preserve the biological activity of the TNF inhibiting antibody so as to be able to treat one or more autoimmune disorders. In specific embodiments, the TNF inhibiting antibody contained in the micro-tablet or other shaped mass may correspond to one or more of adalimumab (Humira), infliximab (Remicade), certolizumab pegol (Cimzia) or golimumab (Simponi), or etanercept (Enbrel). Further description of adalimumab may found at http://en.wikipedia.org/wiki/Adalimumab As various embodiments of the shaped masses described herein comprise TNF antibodies, a brief discussion will now be presented on the TNF inhibitor class of antibodies, the conditions they treat and the mechanism of treatment. Tumor necrosis factor (herein TNF, or TNF-α) is a cytokine involved in systemic inflammation. The primary role of TNF is in the regulation of immune cells. TNF, being an endogenous pyrogen, is able to induce fever, to induce apoptotic cell death, to induce sepsis (through IL1 & IL6 production), to induce cachexia, induce inflammation, and to inhibit tumorigenesis and viral replication. TNF promotes inflammatory response, which in turn causes many of the clinical problems associated with autoimmune disorders such as rheumatoid arthritis, spondylitis, Crohn's disease, psoriasis, hidradenitis suppurativa and refractory asthma. Antibodies that can therapeutically achieve inhibition of TNF-α come under this TNF α (Tumor Necrosis Factor α) inhibitor class of antibodies. All antibodies including this TNFα inhibitory class of antibodies are characterized by having the structure of antibody, which is described as containing two fragments, Fab and Fc, joined together by disulphide bonds to form a Y-shaped molecule. Examples for TNFα inhibitory class of antibodies are: Infliximab (Remicade) is mouse Fab-human Fc chimeric antibody (~150 kda), Adalimumab (Humira©) ~148 kda fully humanized antibody, Etanercept (Enbrel) is 150 kda, p75 TNF-receptor domain-Fc (IgG1) fusion protein, Certolizumab pegol (Cimzia) has human mab (Fab) linked to PEG. The most labile part of an antibody including TNFα inhibitory class of antibodies is the disulphide bonds at the junction of the Y-shape. As shown by the examples herein, the inventors have demonstrated (by virtue ELISA data showing that antibody molecule remains structurally intact and retains its bioactivity) that these disulphide bonds are preserved for various antibodies incorporated into a micro-tablet fabricated using the compression formation methods described herein. Therefore, one skilled in the art will appreciate that embodiments of the compression formation methods described herein would be expected to preserve the structure and bioactivity of antibody (including the TNF inhibitory class of antibodies) which has disulphide bonds at the junction of its Y-shaped molecule.

A description of the formation process for a micro-tablet or other shaped mass comprising adalimumab (herein HUMIRA), will now be provided; however it should be appreciated that this process is applicable to any antibody and in particular to any antibody in the TNF inhibitory class of antibodies (e.g., infliximab or etanercept, etc.). The compression force used to fabricate a micro-tablet containing HUMIRA may be in the range of 1.0 to 4 pounds of force, with a specific embodiment of 3 lbs. The weight percent of the HUMIRA in the mass can be in a range from about 60 to 95%, more preferably from about 80 to 95%, with a specific embodiment of about 95%. The biological activity of the HUMIRA in the shaped mass may be in a range from about 67 to 99% to that prior to formation (e.g. from a powder used to form the micro-tablet). The density of the micro-tablet in such embodiments can range from about 0.86 to 1.05 mg/mm$^3$, more preferably from about 0.88 to about 1.03 mg/mm$^3$. In preferred embodiments, the biological activity of the HUMIRA in the shaped mass may comprise about 86 to 99% of that prior to formation. The density of the micro-tablet in such embodiments can range from about 1.09 to 1.17 mg/mm$^3$. Measurement of the biological activity of the HUMIRA in shaped mass can be performed using assays known in the art, including ELISA or other immuno-assay methods.

According to one or more embodiments, the HUMIRA containing shaped mass may also comprise one or more excipients including, for example, a lubricant, a bulking agent and a binding agent or binder. The lubricant is selected to reduce the amount of force required to eject drug containing shaped masses from a mold and may correspond to polyethylene glycol (PEG) an example including PEG 3350. The bulking agent may correspond to mannitol and the binder may correspond to povidone. The weight percent of PEG can range from about 1 to 15% with a specific embodiment of 10%.

Embodiments of Shaped Masses Comprising Interleukin Inhibiting Antibody.

According to one or more embodiments of the pharmaceutical compositions described herein, the drug contained in the micro-tablet or other shaped mass comprises an interleukin neutralizing antibody or other interleukin neutralizing immunoglobulin or protein wherein the interleukin neutralizing antibody is capable of neutralizing and/or inhibiting the biologic effects of one more of interleukins 1-36 by preventing or diminishing the ability of the selected interleukin from binding to a receptor for that interleukin. Such a neutralizing effect can be achieved by selecting the interleukin neutralizing antibody which binds to the selected interleukin or a receptor for that particular interleukin so as to prevent the interleukin from activating the receptor and in turn causing one or more biologic effects. Related embodiments provide methods of preparing a shaped mass comprising a drug wherein the drug comprises an antibody that neutralizes the biological/biochemical effects of interleukins including interleukins 1-36 wherein the biological activity of the anti-body ((e.g., its binding affinity to a selected antigen and/or neutralizing ability of the selected antigen) is preserved after formation of the shaped mass in amounts of 70, 80, 90 or 95% relative to that of a precursor material prior to formation such amounts considered to comprise substantial preservation of the biological activity of the antibody. Accordingly as used herein, the term "substantially preserved" in reference to the biological activity of an antibody or other therapeutic agents referred to herein means preservation of the biological activity of the particular therapeutic agent in an amount equal to or greater than 70% to that prior to fabrication of the shaped mass and/or prior to insertion of the shaped mass into tissue e.g., intestinal wall or adjacent tissue.

Many embodiments provide shaped masses comprising antibodies which neutralize the biological effects of the interleukin 17 family of interleukins with particular embodiments comprising one or more of the antibodies Seckinumab, Brodalumab, and Ixekizumab. For example, according to one embodiment, the shaped mass can include a therapeutically effective dose of Seckinumab for the treatment of plaque psoriasis which may correspond to a dose in the range of about 3 to 10 mg. In another embodiment, the shaped mass can include a therapeutically effective dose of Brodalumab for the treatment of psoriatic arthritis which may correspond to a dose of about 10 to 20 mg of Brodalumab. In another embodiment, the shaped mass can include a therapeutically effective dose of Ixekizumab for the treatment of psoriatic arthritis which may correspond to a dose of about about 2 to 6 mg of Ixekizumab.

Embodiments of Shaped Masses Produced Using 3 D Printing Methods.

Various embodiments of the invention also provide methods of preparing a shaped mass comprising a drug (which may comprise a protein or polypeptide) wherein an outer coating(s) and/jacket of materials is formed over the drug using 3-D printing methods so as to form a selectively shaped micro-micro tablet or other shaped mass. The coating or jacket may comprise one more biodegradable materials described herein. According to one or more embodiments, the 3-D printing methods can be configured to deposit the coating or jacket as a single layer or as multilayer coating. In the latter case, different layers can be applied which have different compositions, material properties, and thickness. In such multilayer applications allows for more precise control of one or more properties of the shaped including for example the rates of biodegradation of the shaped mass. For example according to one embodiment, a relatively fast degrading layer can be deposited over a drug layer, which is in turn positioned over a more slowly degrading layer that in turn is positioned over a core mass of drug. In use, such embodiments, provide for bio-modal form of release with a rapid release (e.g., a bolus release) of drug under the first layer and a more slow release of drug under the second layer.

Use of 3-D printing methods allow the shaped mass to be formed with minimal or no pressure applied to the mass and in turn the underlying drug. In use, such methods improve the yield of the drug in the final shaped mass due to decreased protein denaturation and/or other degradative effects on the drug. This in turn improves the bioactivity of the drug in the final shaped mass. Use of 3-D printing also allows a variety of shapes to be produced without use of a mold or other related device reducing the potential for contamination and improving sterility.

Such shapes may include for example, an arrow head shape, rectangle, pyramidal, spherical, hemispherical, conical and others. 3 D printing methods also allow for rapid customization of the drug mass shape and size for individual patient parameters, for example one or more of a patient's weight, medical condition and particular medical regimen (e.g. taking of medication once day, twice etc.). In still other embodiments, 3-D printing methods can be used to produce shaped masses configured to have a bimodal form of delivery, e.g. fast release and slow release.

Embodiments of Inventories of Shaped Masses Having Uniform Properties.

Other embodiments of the invention provide an inventory of shaped masses comprising a drug such as a peptide, protein or immunoglobulin, wherein a property of a composition comprising the shaped mass, such as the biological activity of the drug post formation, is maintained within a selected range for substantially the entire inventory. In use, such embodiments help to ensure the uniformity of one or more of dosage, pharmacokinetic parameters (e.g. $t_{1/2}$, $t_{max}$, $c_{1/2}$, $c_{max}$, AUC, MRT etc) and resulting clinical effect for one or more selected drugs delivered using the shaped masses. For example, for embodiments of the shaped mass comprising insulin, the biological activity and/or weight percentage of the insulin post formation can be maintained in a range of about 99.2 to 99.8% to that prior to formation for substantially the entire inventory.

Embodiments of Shapes for the Shaped Masses.

In various embodiments the size and shape of the micro-tablet or other shaped mass can be configured to control and/or optimize one or more of the following parameters: the payload (e.g., mass) of drug, shape and size of the particular tissue penetrating member, size of the delivery capsule (containing and/or otherwise carrying the tissue penetrating member comprising the shaped mass), pharmacokinetic parameters (e.g., $C_{max}$, $C_{1/2}$, $t_{max}$, $t_{1/2}$) and the release rate of drug. According to one or more embodiments the micro-tablet can have a cylindrical, capsule (e.g. hot dog), rectangular, spherical, hemispherical, dogbone or triangular volumetric shape. In preferred embodiments, the micro-tablet has a cylindrical or like shape with a diameter in the range of about 0.5 to 1.5 mm and a length of about 1 to 4 mm. These and other shapes for the shapes for embodiments of the shaped masses 10 are shown in FIGS. 1-11.

Embodiments of the Shaped Masses in the Form of Spherical Drug Beads.

In various embodiments, the shaped mass can be in the form bead or micro-bead which is inserted or otherwise formulated into embodiments of a tissue penetrating member described herein. Multiple such beads may be formulated into the tissue penetrating member, with different beads formulated to have different drug release so as to achieve and/or comprising different drugs. In use, such embodiments allow for the simultaneous delivery of multiple drugs (e.g. such as those used to in a multidrug regimen to treat a particular condition such as AIDS, autoimmune disease (e.g., MS) as well as achieve a varied or release profile and release rate of drug. For example, in one or more embodiments, the beads cans be selected to achieve a biomodal release profile for a particular drug. For embodiments of beads having varied release rates, beads can be included in the tissue penetrating member which have a fast release period (e.g., minutes to hours) and a slower release profile (e.g. hours to days). In use, such fast and slow release drug bead embodiments allow for a rapid rise in plasma concentration of drug so as to quickly approach therapeutic levels for the drug and a slower release to keep the plasma concentration at the therapeutic level for extended periods of time (e.g., days to week) once the release from the faster releasing bead tails off. In related embodiments, additional beads can be included which have an intermediate release rate (e.g. in between the fast and slow release rate) so as to achieve a more constant drug concentration over an extended period of time, for example, over a period from a few hours to 14 or thirty days or more.

Several different approaches are contemplated for achieving varied drug release rates and profiles for embodiments using drug beads. According to one or more embodiments, the varied release profiles can be achieved by formulating the beads with embodiments of water-soluble polymer and/or drug sequestering polymers described herein. According to other embodiments the surface area of the bead can be used to control the release rate. Multiple smaller beads can be used to produce faster release rates and larger beads can be used to produce a slower though a longer lasting release of drug. The rates of drug release for particular bead sizes can be determined using the Noyes-Whitney equation (shown below) to calculate the rate of drug dissolution from the bead into the interstitial fluids of the intestinal wall or other target tissue site.

$$\frac{dW}{dt} = \frac{DA(C_s - C)}{L}$$

Where:

$\frac{dW}{dt}$ is the rate of dissolution.
A is the surface area of the solid.
C is the concentration of the solid in the bulk dissolution medium.
$C_s$ is the concentration of the solid in the diffusion layer surrounding the solid.
D is the diffusion coefficient.
L is the diffusion layer thickness.

Applying this equation to an embodiment having three beads, two smaller and one larger bead having a radius of 1 mm, where the two smaller beads having the same total mass as the third larger bead, owing to their larger surface area, the two smaller beads are going to produce a release rate that is about 26% faster than the larger sphere. Other embodiments contemplate a variety of mixtures of smaller and larger beads so as to achieve a desired drug distribution profile e.g. biomodal, trimodal etc. over a selected time period for a particular drug or drugs. For example, in one embodiment, the shaped mass can include two 0.8 mm beads (for fast drug release), one 1 mm bead (for mid-rate release) and a third 2 mm bead for longer term release. Also according to one or more embodiments, the rate of release can be further increased (e.g., per the Noyes-Whitney equation) by texturing the surface of the bead (or other shaped mass) so as to increase its surface area relative to unshaped beads. Texturing of the bead surface can be achieved using a variety of known methods, e.g. by the use of textured molds and/or plasma treatment of the beads. In various embodiments, texturing of the bead surface can be done to increase its surface area from 5 to 300% or more, with specific embodiments, of 25, 50, 75, 100, 125, 150, 175, 200, and 250% increase in surface area.

Embodiments of the Shaped Masses Including Salts.

In various embodiments, the shaped mass can also comprise one or more salts which are selected for various properties which affect the shaped mass and/or the drug. In particular embodiments, the salts are selected to stabilize the drug molecule and adjust the pH of the shaped mass once positioned in situ in the wall of the small intestine or other location. Such pH adjustment can be used to control the elution profile of the drug. For example, for a drug such as long acting insulin, low pH can be used to promote the formation of multi-meric insulin micelles which slowly dissociate at the tissue boundary of the micelles to form monomers which comprise the bioactive form of the drug such as the monomer form of insulin. Suitable acids in salt form to be used into the shaped mass can include ascorbic acid, citrates, hydro chlorates, EDTA, sodium acetate and all like salts. Suitable bases in salt form to be used in the shaped mass can include hydroxides, chloride (sodium chloride, potassium chlorides), phosphates (potassium phosphates, sodium di-hydrogen phosphates) carbonates, bicarbonates, azides and all like molecule.

Embodiments of the Shaped Mass Including Drug Sequestering Polymers.

In various embodiments, in addition to the API, the shaped mass can also comprise one or more repeating chain complexes herein in drug sequestering polymers 41 also described as a ds-polymer 41 configured to trap or otherwise contain (e.g., by binding) the drug molecules (e.g., polypeptide, protein or other API) within the polymeric structure formed by the repeating chains.

In various embodiments, the ds-polymer may correspond to one or more of water swellable polymers such as various hydrogels PEG (polyethylene glycol, of various molecular weights), dextrin, cyclodextrin, dextran, cyclo-dextran, mannitol and other complex sugars, cellulose, methyl-cellulose and other like molecules. One or more of the ds-molecules are mixed with the API into the shaped mass in ratios in a range from about 3:98 to about 98:2. For example, for embodiments of the micro-tablet comprising PEG and Immunoglobulin-gamma (IgG) or other antibody the weight ratio of PEG to the mass of an immunoglobulin can be in the range of about 1:2 to about 1:49. For embodiments of the micro-tablet comprising PEG and insulin (or other comparable protein), the weight ratio of PEG to the mass of insulin can be in the range of about 1:1 to about 1:19. For embodiments of the micro-tablet comprising Povidone and insulin, the weight ratio of Povidone to the mass of insulin can in be in the range of about 1:19 to about 1:99. For embodiments of the micro-tablet comprising mannitol and insulin, the ratio of the mass of mannitol to the mass of insulin can be in the range of about 1:1 to about 1:9.

Embodiments of the Shaped Masses Including Drug Sequestering Water Swellable Polymers.

Figure 12B:
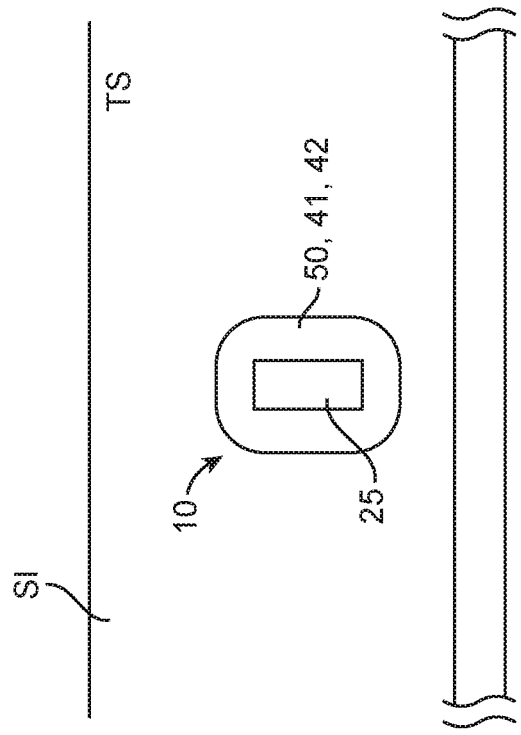
FIGS. 12a-12d are lateral views illustrating use of swellable polymers to create a barrier structure to contain the release of a drug or other therapeutic compound delivered by embodiments of the tissue penetrating member.
Figure 12A:
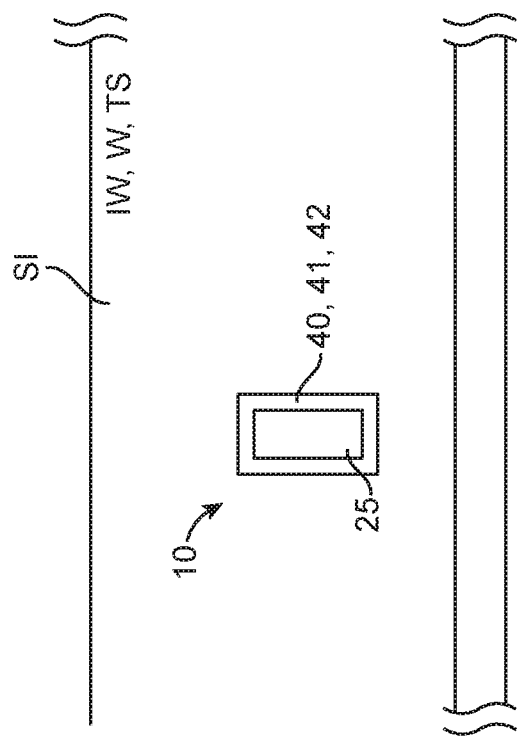
Figure 12C:
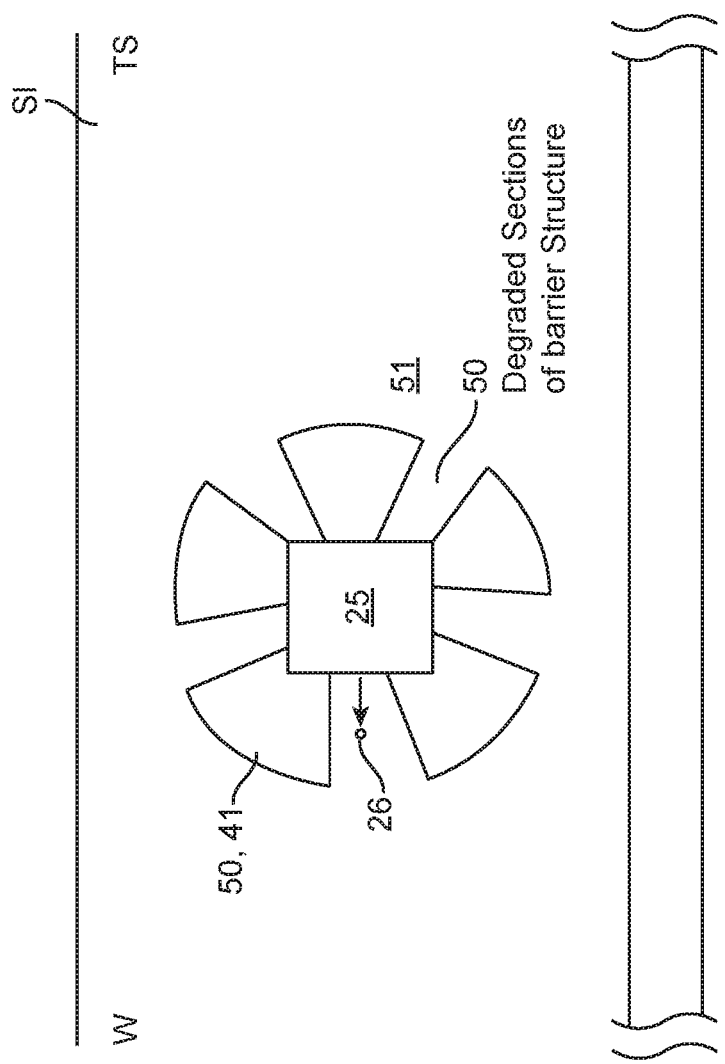
Figure 12D:
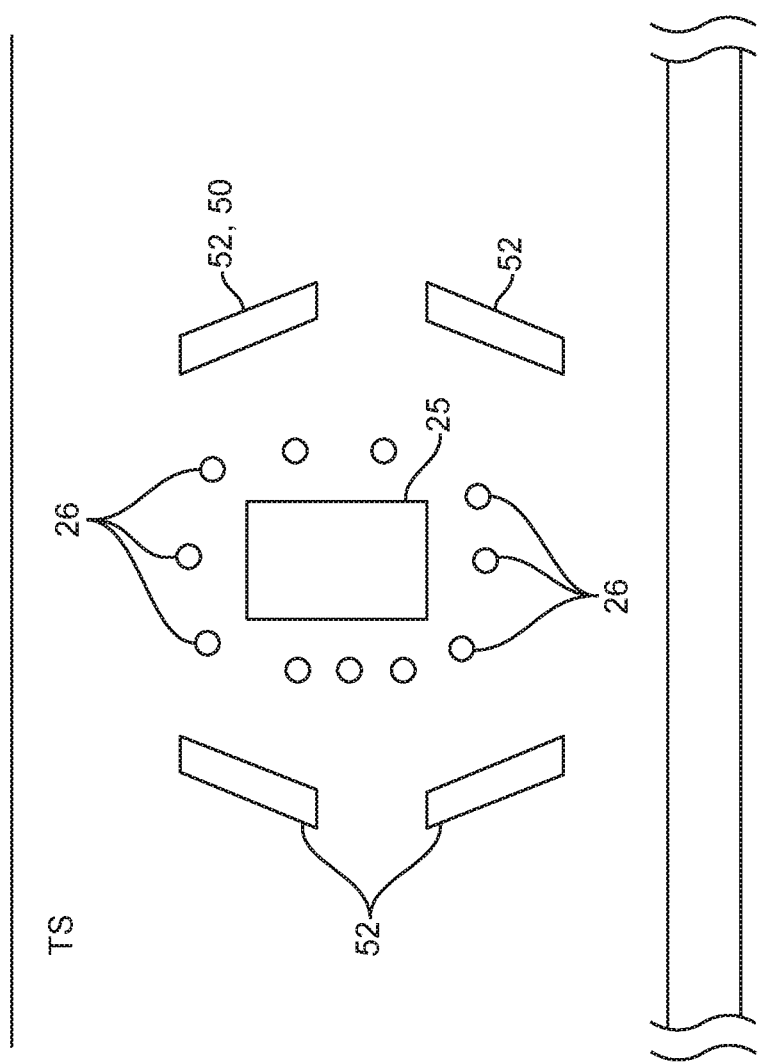

In various embodiments, the shaped mass can include ds-polymers 41 which comprise one or more water swellable polymers 42 (herein ws polymers 42) such as various hydrogels which function to create a barrier structure 50 described herein. The function of an embodiment of such a barrier structure will now be described. Referring now to FIGS. 12a-12d, once the shaped mass 10 is inserted into a moist tissue environment such as that found in the wall W of the small intestine SI, the polymer chains of the ds-polymer may expand or otherwise, reshape or re-orient to form a three dimensional structure or barrier structure 50 as shown in FIGS. 12a and 12b, to further contain and control the release of the API 25. The barrier structure 50 is subsequently biodegraded (e.g., by hydrolysis) within the intestinal wall (or other location) as shown in FIGS. 12c and 12d which in turn causes the release of drug or API. FIG. 12c illustrate the degraded sections 51 of the barrier structure allowing tissue fluid to reach the API 25 allowing molecules 26 of the drug 25 to be absorbed or otherwise diffuse into tissue at the tissue site TS. FIG. 12d shows the barrier structure 50 completely degraded with only remnant sections 52 (which are further degraded or pass through the intestinal tract) allowing more significant amounts of diffusion or transport of the drug molecules 26 into the tissue site TS. In particular embodiments, when the barrier structure 50 is present, the API 25 can have a first rate of release and is it degrades it may have a second rate of release which typically will be faster than the first rate of release. In this way, one or more ds-polymers can be used to control the drug elution/release profile in a predetermined predictable fashion. In particular embodiments, based on the type and amount of the water swellwable polymer 42 or other ds-molecule 41, the rate of release of the API can be slowed relative to an API release rate when the ds-polymer is not present in a range from about 10 to 300% or even higher such as 500 to 1000%. Narrower reduction range may include 20 to 300%, 20 to 250%, 20 to 150%, 20 to 100, 50 to 250% 50 to 150% and 50 to 100%. Specific embodiments for reduction of the release rate may include 20, 30, 50, 75, 100, 150, 200, 225, 250 and 275%. Slower release rates can be obtained for the use of three dimensionally structured ds-polymers such as various cyclical shaped ds-polymers (e.g., various) cylcodextrins, and/or ds-polymer having larger molecular weights. For example, using one more of these or other ds-polymers, the release rate of an API such as insulin, a TNF-alfa antibody or an interleukin neutralizing antibody can be slowed in the range of 1 mg/per minute to 1 mg per hour so that for a 5 mg dose of drug the release time can be extended from approximately five minutes to approximately 5 hours.

The ws-polymers 42 are desirably formulated into the shaped mass in a dry state and then when exposed to the moisture in tissue (e.g. from interstitial fluids when the shaped mass is inserted into the intestinal wall) swell to form an in situ three dimensional structure also referred to herein as barrier structure which entraps or otherwise contains the drug (e.g. by intercalating with the drug molecules) to form a reservoir or depot of drug from which the drug elutes in a predictable, pre-determined time course, e.g., several hours to several days or longer. The water swellable polymer 42 can include those known in the art and in preferred embodiments comprise hydrogels. Suitable hydrogels can include both natural polymer and synthetic polymer hydrogels and combinations of both. They also may be in the superabsorbent and super-porous class of hydrogels or both. Further description of suitable hydrogels and their properties may be found in the paper by E Ahmed, entitled "Hydrogel: Preparation, characterization, and applications: A review" Journal of Advanced Research (2015) 6, 105-121 the contents of which are incorporated by reference herein for all purposes. After the hydrogel or other barrier structure 50 forms, it can be configured to subsequently biodegrade over a selected period at the tissue site so as to release the drug or other therapeutic agent as is shown in FIGS. 12c and 12d. The degradation can be by one or more of hydrolysis or other chemical reaction of various bonds of the water swellwable polymer such as various cross links. Depending upon the hydrogel and its properties (e.g. molecular weight, degree of cross linking) and amount of hydrogel in the shaped mass, the period of degradation can be in the range of 4 hours 7 days, with specific embodiments of 6, 8, 12, 24, 36, 48, 72, 96, 120 and 144 hours In various embodiments, the amount of hydrogel or other ws-polymer 42 can range from about 4 to 98% weight percent of the shaped mass 10 with specific embodiments of 10, 20, 30, 40, 50, 60 and 75 weight percent. The amount being selected to control one more of the degree of swelling and the selected period of release of the drug. According to various embodiments the hydrogel or other ws-polymer can be selected so as to swell between 10 to 100 times in volume of its dry form volume so as to cause the shape mass to swell in a similar amount in volume. According to some embodiments, the amount of swelling is sufficient to fix or anchor the shaped mass in place in the wall of the small intestine or other target tissue site. The amount of swelling to achieve such an anchoring function can be in the range of 3 to 50 times. In particular embodiments, the hydrogel or other ws-polymer can be configured to cause the shaped mass to swell from a length of 3 about mm and a diameter of about 0.7 mm to a length of 30 mm and a diameter of about 7 mm.

Embodiments of the Shaped Mass Including Drug Sequestering CycloDextrins.

Referring now to FIGS. 13-17, in various embodiments, the drug sequestering polymer 41 may comprise a polymer 43 which non-covalently and reversibly interacts with the drug so as to slow a release rate of the drug from the shaped mass into tissue surrounding the shaped mass such as intestinal wall and/or peritineal wall tissue once the shaped mass 10 is placed there. Such reversible non-covalent interactions can comprise one or more of electrostatic Coulomb, dipole-dipole, van der Waals, solvophobic, hydrophobic, or hydrogen bonding interactions or other supramolecular chemical interactions. In many embodiments, such drug sequestering polymers 43 can include compounds having a cavity typically a hydrophobic cavity which reversibly interacts with the drug in the presence of aqueous tissue fluids (e.g., various interstitial fluids) surrounding the shaped mass 10 to form a reversible inclusion complex 70 comprising the drug 25 and the drug sequestering polymer 41. The complex also known as an inclusion compound 70 can be configured to be reversible based in part on a change in the chemical, fluidic or other physical property in the fluid dissolving or otherwise surrounding the host-guest complex. Such changes in the physical properties can include, for example, a change in the pH of the fluid (e.g. an increase in pH from about 7 to a neutral pH) and or a change in the concentration of the inclusion compound (e.g., a decrease in the concentration as inclusion compound diffuses down gradient and/or more dilute aqueous tissue fluids are drawn to the host guest complex by osmolar gradient, hydrophilic or other related forces).

Figure 13:
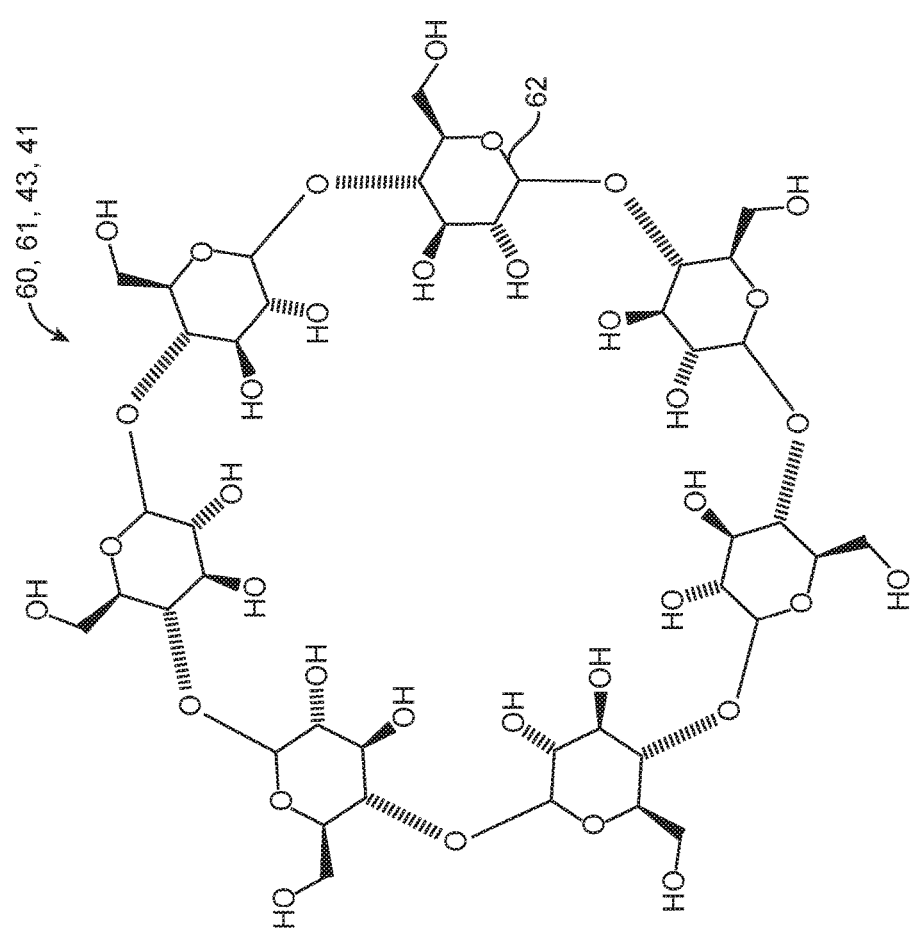
FIG. 13 shows the chemical structure of a cyclodextrin molecule.
Figure 14A:
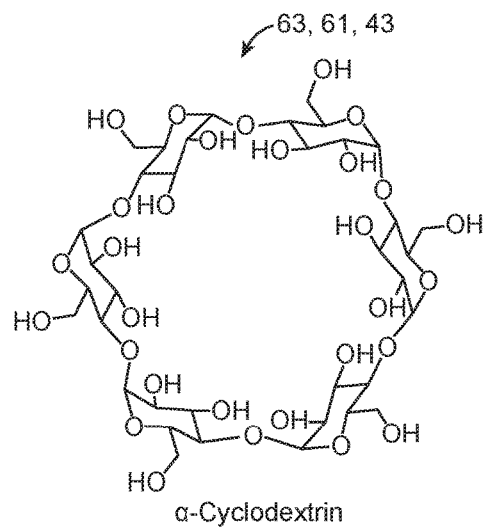
FIG. 14a-14c shows embodiments of the chemical structure of various cyclodextrins molecules including alfa (FIG. 14a), beta (FIG. 14b) and gamma (FIG. 14c) cyclodextrins
Figure 14B:
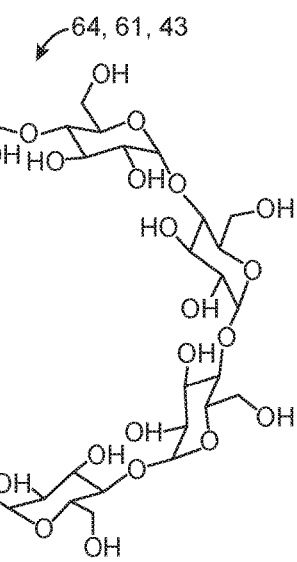
Figure 14C:
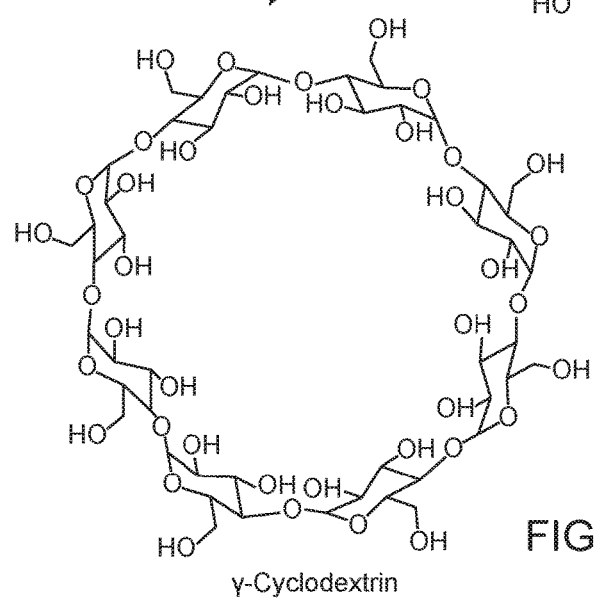

In the above and related embodiments, the drug sequestering polymer 41 may comprise cyclic oligosaccharides 60, including various cyclodextrins 61 comprising 5 or more α-D-glucopyranoside units 62. An example of the chemical structure of a cylodextrin one or more α-D-glucopyranoside units 62 is shown in FIG. 13. Cyclodextrins (also known as cycloamyloses) are a family of compounds made up of sugar molecules bound together in a ring (i.e., cyclic oligosaccharides). Cyclodextrins are produced from starch by means of enzymatic conversion. They are composed of 5 or more α-D-glucopyranoside units 61 linked 1→4, as in amylose (a fragment of starch). The largest well-characterized cyclodextrin contains 32 1,4-anhydroglucopyranoside units, at least 150-membered cyclic oligosaccharides are also known. Typical cyclodextrins contain a number of glucose monomers ranging from six to eight units in a ring, creating a cone shape. As shown in FIGS. 14a-14c, according to one or more embodiments, suitable six to eight unit cyclodextrins 61 may correspond to one of the following molecules: α (alpha)-cyclodextrin 63, a 6-membered sugar ring molecule; β (beta)-cyclodextrin 64, a 7-membered sugar ring molecule; and γ (gamma)-cyclodextrin 65, a 8-membered sugar ring molecule. Still other cyclodextrins are considered. In preferred embodiments the cyclodextrin comprises the β (beta)-cyclodextrin form as the cavity of this particular cyclodextrin has a size for accommodating a variety of drugs and other therapeutic agents such as various hormones and vitamins.

Figure 15B:
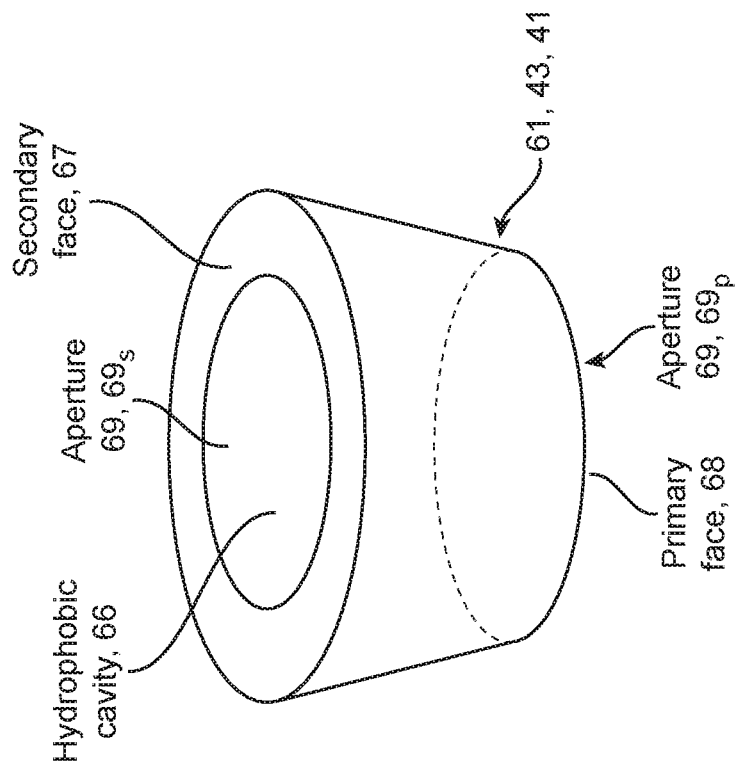
FIGS. 15a and 15b show the chemical and three dimensional structure of a cyclodextrin molecule.
Figure 15A:
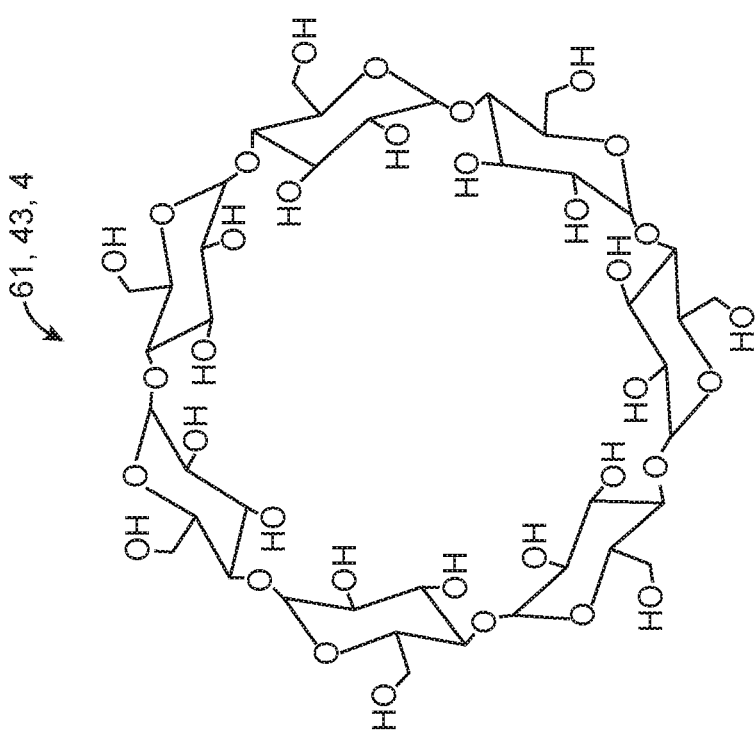

Typically, cyclodextrins have a toroid shape with a hydrophobic cavity 66 and the secondary and primary faces 68 and 67 (which consist of what are known as the primary and secondary groups of exposed hydroxyl groups) which define two openings or apertures including a larger and smaller aperture 69s and 68p also known as the secondary (the larger) and primary apertures 69 as is shown in FIG. 15b. The hydrophobic cavity 66 is what interacts with one or more drugs 25 to form the inclusions compound 70 (by one or more super-molecular interactions, e.g., hydrophobic, hydrogen bonding interactions, etc.) and its size (e.g., the primary or secondary opening size) can selected to complex with specific drugs or other therapeutic agents.

Complexation of Cyclodextrins (CD) with Drug:

Complexation of molecules to CDs occurs through a non-covalent interaction between the molecule and the CD cavity. This is a dynamic process whereby the guest molecule continuously associates and dissociates from the host CD. CDs are insoluble in most organic solvents; they are soluble in some polar, aprotic solvents. Although the solubility of CDs is higher in some organic solvents than in water, complexation may not occur readily in non-aqueous solvents because of the increased affinity of the guest for the solvent compared to its affinity for water. Also CDs form complexes with lipophilic solvents, even with ethanol and methanol, and these complexes become contaminants in the final product. CDs glass transition occurs at about 225 to 250° C. The glass transition temperature varies with the degree of substitution. Thermal decomposition occurs at 308° C. Strong acids such as hydrochloric acid and sulfuric acid hydrolyze CDs. The rate of hydrolysis is dependent upon temperature and concentration of the acid. CDs are stable against bases. HP-CD can be hydrolyzed by some amylases at a very slow rate compared to the corresponding unsubstituted CD. The greater the degree of substitution, the less hydrolysis occurs. Substitution provides hindrance to the binding of CD to the active site of the enzyme; as a result, the extent of hydrolysis is reduced.

THE MECHANISM OF DRUG RELEASE FROM CD COMPLEXES: Different mechanisms play a role in drug release from the drug-CD complex. Complexation of the drug (D) to CD occurs through a non-covalent interaction between the molecule and the CD cavity. This is a dynamic process whereby the drug molecule continuously associates and dissociates from the host CD. Assuming a 1:1 complexation, the interaction will be as follows:

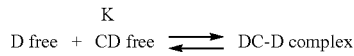

Two parameters, the complexation constant (K) and the lifetime of the complex factor into the drug release mechanism.

Dilution.—Dissociation due to dilution appears to be a major release mechanism. The recent example reported for miconazole, a more strongly bound drug compared to prednisolone supports the probable role of dilution. Dilution is minimal when a drug-CD complex is administered ophthalmically. Efficient corneal absorption is further exacerbated by contact time.

Competitive Displacement.—Competitive displacement of drugs from their CD complexes probably plays a significant role in vivo. Addition of parabens to parenterals not only leads to decreased antimicrobial activities of the parabens, due to complexation, but also decreases the drug solubility due to its displacement from complexes. showed that alcohol displaces 2-napthol from –CD complexes. It has been reported that the –CD complex of a poorly water-soluble drug, cinnarizine, was more soluble in vitro than cinnarizine alone. Oral administration of the complex showed less bioavailability than expected, based on the in vitro dissolution experiments. It was suggested that cinnarizine was too strongly bound to the CD so that complex dissociation was limiting oral bioavailability. Co-administration of phenylalanine, a displacing agent, improved the bioavailability of cinnarizine from the complex but not from conventional cinnarizine tablets.

Protein binding.—Drug binding to plasma proteins may be an important mechanism by which the drug may be released from a drug-CD complex. It is evident that proteins may effectively compete with CDs for drug binding and thus facilitate the in vivo release of drugs from drug-CD complexes. Dilution alone may be effective in releasing free drugs from weak drug-CD complexes but when the strength of the binding between the drug and CD is increased, a mechanism such as competitive displacement is at work. Plasma and tissue protein binding may also play a significant role. Researchers studied the effect of HP-CD on the displacement of both naproxen and flurbiprofen from plasma binding sites in vivo. They found that tissue distribution of flurbiprofen and naproxen was higher when HP-CD-drug solution was administered compare to drug solution in plasma, 10 minutes after parenteral dose, meaning that more drug was free from CD solution to distribute to the tissues than from the plasma solution.

Drug uptake by tissue.—A potential contributing mechanism for drug release from CD is preferential drug uptake by tissues. When the drug is lipophilic and has access to tissue, and is not available to the CD or the complex, the tissue then acts as a "sink", causing dissociation of the complex based on simple mass action principles. This mechanism is more relevant for strongly bound drugs or when the complex is administered at a site where dilution is minimal, e.g., ocular, nasal, sublingual, pulmonary, dermal or rectal sites. For example, CD has been used in ophthalmic delivery of poorly water-soluble drugs to increase their solubility and/or stability in the tear fluid, and in some cases to decrease irritation.

Figure 16A:
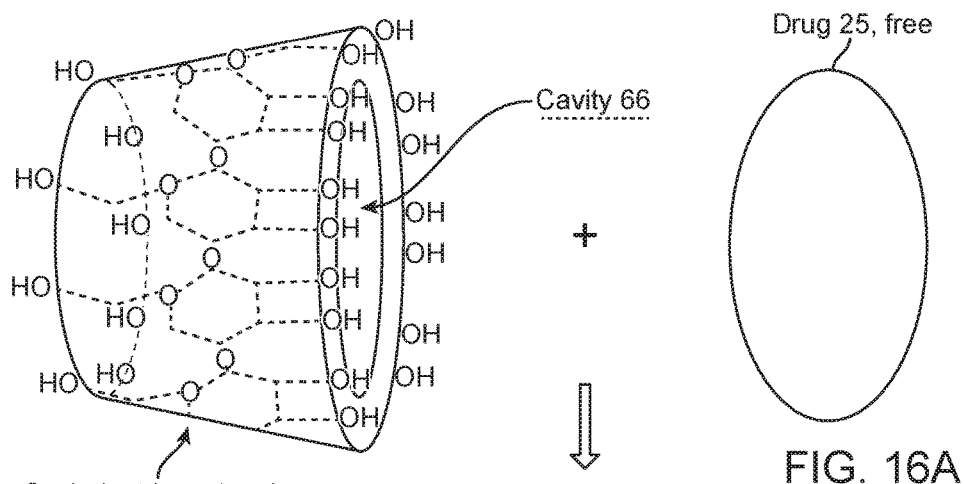
FIGS. 16a-16c are schematic views showing the formation of an inclusion complex (or inclusion compound) between a cyclodextrin molecule and a drug.
Figure 16B:
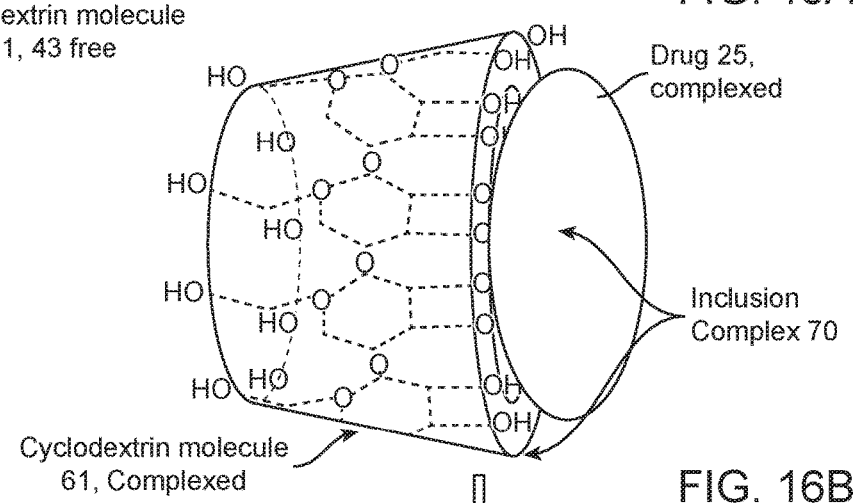
Figure 16C:
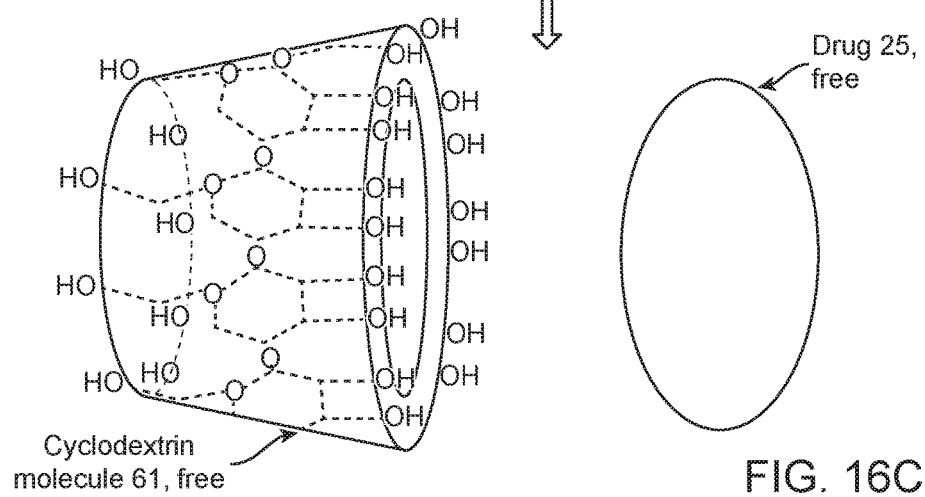

FIGS. 16a-16c illustrate the formation of the inclusion complex or compound 70. Once the drug 25 and cyclodextrin 61 are in the moist tissue environment such as that in the wall of the small intestine the cyclodextrin 61 interacts with the drug 25 in the presence of the aqueous solutions in the wall of the small intestine or other tissue site to have the drug be attracted and then complex with the cavity 66 to form the inclusion compound/complex 70. Then when the pH or dilution of the inclusion compound changes the drug is release where it can then be release into tissue. As shown in FIGS. 17a and 17b according to various embodiments, the drug can be either singly or doubly complexed with cyclodextrin or the other related ds-molecule to form a 1:1 drug-CD (cyclodextrin) inclusion complex 71 or a 2:1 drug-CD (inclusion complex 72. The degree of complexing can be controlled by the ratio of Cyclodextrin to drug, for example a 2:1 ratio or greater.

As indicated, cyclodextrins are capable of forming inclusion compounds 70 with a variety of drugs. The formation of the inclusion compounds greatly modifies the physical and chemical properties of the guest molecule, mostly in terms of water solubility. In particular inclusion compounds of cyclodextrins 70 with hydrophobic molecules are able to penetrate body tissues, these can be used to release biologically active compounds under specific conditions. In many embodiments mechanism of controlled degradation of such complexes can be based on pH change of water solutions surrounding the inclusion compound 70, leading to the loss of hydrogen or ionic bonds between the host 61 and the guest molecules (the drug 25). In alternative embodiments, other means for the disruption of the complexes take advantage of body heat or action of enzymes added as excipients to shaped mass 10 and/or therapeutic preparation 20 which are able to cleave linkages between glucose monomers.

The reversible interactions between the cyclodextrin 61 or other related drug sequestering polymer 41, 42 or 43 can be selected to slow or otherwise control the release of the drug into the tissue surrounding the shaped mass relative to the release rate of the drug were the drug sequestering polymer not there. In various embodiments, the ratio of the drug sequestering polymer to drug can be selected to decrease the release rate of the drug by selectable amounts (e.g., by 50, 100, 150, 200, 250, 500% etc.). In various embodiments, the ratio of drug sequestering polymer to drug can be in the range of 4:1 to 1:4 with narrower range of 2:1 to 1:2 and specific embodiments of 2:1, 3:2, 1:1, 2:3 and 1:2. The ratio can also be selected such that two or more drug sequestering polymer interact with each drug molecule (e.g., via a ratio of drug sequestering polymer to drug of 2:1).

In additional or alternative embodiments the cyclodextrin molecule 61 can be covalently copolymerized with one or more water soluble polymers such that the resulting copolymer contains multiple cyclodextrin groups which can each bind with a drug molecule. This allows for a single copolymer molecule containing the CD groups to bind to multiple drug molecules allowing for lower ratio of cyclodextrin containing drug sequestering molecule to drug molecule in the shaped mass. For example, various cyclodextrins can be co-polymerized with N-isopropylacrylamide (NIPAAM) as shown in a paper by Jiawen Zhou and Helmut Ritter entitled Cyclodextrin Jiawen Zhou *Polym. Chem.*, 2010, 1, 1552-1559 which is incorporated by reference herein for all purposes so as to have multiple cylcodextrins attached to a single polymer chain Routes of Delivery for the Shaped Masses.

Embodiments of the micro-tablets or other shaped mass described herein, can be configured to be used in combination with any suitable drug delivery system to be administered via any appropriate route of administration. Such routes of administration can include without limitation, oral, sublingual parenteral, intravenous, intramuscular, subcutaneous, intra-ventricular, intra-cardiac, intra-cerebral. For example, according to one embodiment, insulin comprising micro-tablets can be taken orally and then have the drug be absorbed through the wall of the small intestine or delivered into the wall small intestine. In the latter case, this can be done using a drug delivery device which includes a biodegradable tissue penetrating member which contains or otherwise includes the micro-tablet.

The tissue penetrating member may be advanced into the intestinal wall using an advancement means such as an inflatable balloon which directly or indirectly applies a force to the tissue penetrating member. In an alternative or additional embodiment, the micro-tablet can be delivered subcutaneously to an intramuscular or other subcutaneous tissue site. In specific embodiments, the micro-pellet can be configured to dissolve at a selectable rate or rates to achieve a $C_{max}$ or other desired pharmacokinetic parameter (e.g. $t_{max}$ etc.). Further, the composition and properties of the micro-tablet can be configured to have a dissolution rate configured to achieve the desired $C_{max}$ for the tissue at a given site (e.g. in the wall of the small intestine, vs an intramuscular site). In particular embodiments, the shaped mass can be inserted into a cavity in the tissue penetrating member which is then sealed up. The tissue penetrating member may comprise any number of biodegradable materials such as maltose, sucrose or other sugar, PGLA (Polyglycolic lactic acid), polyethylene and others as is described in more detail above.

EXAMPLES

Various embodiments of the invention are further illustrated with reference to the following examples. It should be appreciated that these examples are presented for purposes of illustration only and that the invention is not to be limited to the information or the details therein.

Example 1: Micro-Tablets Comprising Human IG and PEG

Materials.

Pure human IgG (Alpha Diagnostics Intl. Inc, Cat#20007-1-100), Poly Ethylene Glycol 3350 (PEG, Sigma-Aldrich, Cat#P4338-500G), Water, molecular biology reagent grade (Sigma-Aldrich, Cat#W4502).

Methods.

Human IgG and PEG 3350 in powder form were weighed out and mixed into a solution using molecular biology reagent grade water. The percentage of IgG and PEG are 90% and 10% respectively and the powders were dissolved in water at 40 mg/ml concentration. Batches using different IgG mass capacity were prepared: 100 mg (batch 6 and 7), 140 mg (batch 8) and 60 mg of IgG (batch 9). The aqueous solution was placed in a silicone plate and then evaporated in a vacuum chamber with desiccant inside of a refrigerator for a minimum of 19 hours (batch 6, 7 and 8) and up to 21 hours (batch 9) until full evaporation occurs. Data for batches 1-5 are not included because these batches were trial batches made using a different processes (e.g. different or no milling, evaporation, etc.) and micro-tablets were not fabricated for some of these batches as well The evaporated powder was collected into a low-bind conical 1.5 ml tube. Two small stainless steel balls (3.96 mm diameter, 0.5 g total mass) and a rotator (Roto-shake Genie) at max speed were used for milling. The milling duration was 1.75 hrs (batches 6 and 7) and 1.5 hours (batches 8 and 9). It was done at 64° F. room temperature with an ice pack surrounding the tube Once the powder was milled, micro-tablets were fabricated using a semiautomatic molding fixture. The molding parameter included a compressive force of approximately 2.5 to about 3.5 lbs of force and a compression hold time of approximately 3 sec. Measurements were made of the amount of intact (e.g. biological active) IgG that was recovered in the powder from before-milling, after-milling and in the formed micro-tablets. These measurements were made using IgG immunoassay (Alpha Diagnostics Inc.).

Micro-tableting includes the steps of processing of the powder recovered from evaporation into fine homogenous powder and then forming it into a solid micro-tablet. The before-milling powder recovery is the starting point of the micro-tableting process and the percentage of IgG recovered using this manufacturing method was calculated by taking the before-milling protein recovery (e.g., the amount of biologically protein active recovered in the powder prior to milling) to be 100%. The micro-tablet data and IgG recovery values are detailed in Table 1. Densities were measured by measuring the mass and volume of the tablet. Average density was found to be between 1.02 and 1.06 mg/mm3 while the recovery of intact and bioactive IgG found in the micro-tablets was equal or higher than 94.2% in average.

TABLE 1

Micro-tablet Data and IgG recoveries for IgG Micro-tablets comprising 90% IgG and 10% PEG 3350.

| IgG Batch #* | Micro-tablet Length (mm) | Micro-tablet Weight (mg) | Micro-tablet Density (mg/mm$^3$) | Absolute Micro-tablet IgG Recovery |
|---|---|---|---|---|
| 6 | 2.77 ± 0.07 (N = 23) | 1.16 ± 0.03 (N = 23) | 1.05 ± 0.01 (N = 23) | 87% ± 1.4% (N = 10) |
| 7 | 3.17 ± 0.15 (N = 15) | 1.33 ± 0.06 (N = 15) | 1.06 ± 0.02 (N = 15) | 94.1% ± 0.9% (N = 5) |
| 8 | 2.67 ± 0.09 (N = 15) | 1.11 ± 0.03 (N = 15) | 1.06 ± 0.02 (N = 15) | 89.2% ± 3.2% (N = 5) |
| 9 | 2.85 ± 0.09 (N = 13) | 1.15 ± 0.02 (N = 13) | 1.02 ± 0.02 (N = 13) | 77.8% ± 1.6% (N = 4) |

Example 2: Micro-Tablets Comprising Human IgG PEG and Other Excipients

Materials.

Pure human IgG (Alpha Diagnostics Intl. Inc, Cat#20007-1-100), Poly Ethylene Glycol 3350 (PEG, Sigma-Aldrich, Cat#P4338-500G), Water, molecular biology reagent grade (Sigma-Aldrich, Cat#W4502), sodium chloride (Sigma-Aldrich, Cat#S9888), mannitol (Sigma-Aldrich, Cat#M8429-100G).

Methods.

Human IgG was dissolved along with lubricant PEG 3350 and principal excipients in HUMIRA pen (sodium chloride and mannitol) in the same percentage that in the pen solution. The powders were brought into solution using 0.94 ml of molecular biology reagent grade water. The evaporation process was done using the same procedure as used in a) above.

The evaporated powder was then transferred to a low-bind round-bottom 2 ml tube. The milling process was slightly different for each batch. Batches 7 and 8 were milled using stainless steel ball having a mass of 0.438 with 3 hours of milling. Batch nine was made using a an Yttrium-stabilized zirconium ball having a mass of 0.454 gr with a milling duration of 3 hours. The rotation method and temperature conditions were kept as used in example 1). Note, data for batches 1-6 are not included because they were made for milling optimization purposes only and micro-tablets were not fabricated for these batches. Approximate measurements were made of particle grain sizes (diameter or widest dimension) for cases 7, 8 and 9 using a hemocytometer. Particle size ranged from about 50 to about 450 µm for the three batches with specific data of 100, 200, 200, 400 and 400 for batch 7; 50, 200, 300 and 400 for batch 8; and 50, 100, 300 and 450 for Batch 9.

After milling, micro-tablets were fabricated using an automatic fixture using compression forces 2.6 lbs. of compression force and a compression holding time of 3 sec. The intact IgG recovered from the stages of before-milling powder, after-milling powder and micro-tablets were tested using an IgG immunoassay (Alpha Diagnostics Inc.). The micro-tablet data and IgG recovery values are detailed in Table 2.

Definitions for Terms Used in Tables

The definitions for the terms used in the tables below is provided below.

Absolute Protein Recovery after Micro-Tableting (APRAMT):

This is the percentage of active protein in the micro-tablet relative to that amount in the powder used to form the micro-tablet; it is determined using an ELISA assay of the selected protein in the micro-tablet. The formula for calculation of this value is shown below APRAMT=(ELISA estimated protein content mass in the micro-tablet)/(total micro-tablet mass*protein mass percentage in total mass)

Example 3: Micro-Tablets Comprising HUMIRA and HUMIRA Pen Excipients

Materials.

HUMIRA pens (Abbott Laboratories) and Poly Ethylene Glycol 3350 (PEG, Sigma-Aldrich, Cat#P4338-500G).

Methods.

The solution contained in the HUMIRA pen was placed in a low-bind 1.5 ml tube where PEG 3350 amount was added and mixed with HUMIRA ingredients. The solution was evaporated following the same conditions as the ones described in example 1 a) and b).

The milling conditions were the same as in example 1 a) where two balls were used with total mass of 0.5 grams and

TABLE 2

Micro-tablet Data and IgG recoveries in IgG Micro-tablet

| | | | Formulation | | | |
|---|---|---|---|---|---|---|
| | | 67.8% IgG | 7.5% PEG 3350 Micro-tablet | 8.4% NaCl Micro-tablet | 16.3% Mannitol | |
| IgG Batch # | Milling Ball | Total Ball Mass (grams) | Micro-tablet Length (mm) | Micro-tablet Weight (mg) | Micro-tablet Density (mg/mm$^3$) | Absolute Micro-tablet IgG Recovery |
| 7 | 1 S. Steel | 0.438 | 3.23 ± 0.15 (N = 8) | 1.25 ± 0.07 (N = 8) | 0.97 ± 0.01 (N = 8) | 89.3% (N = 2) |
| 8 | 1 S. Steel | 0.438 | 2.5 ± 0.21 (N = 5) | 1.1 ± 0.07 (N = 5) | 1.12 ± 0.02 (N = 5) | 96% (N = 2) |
| 9 | 1 Zirconium | 0.4539 | 2.76 ± 0.14 (N = 5) | 1.29 ± 0.05 (N = 5) | 1.18 ± 0.01 (N = 5) | 94% (N = 2) |

1.5 hours (batch 1, 2 and 4) and 1.75 hours (batch 3) of milling duration. The same temperature conditions were kept as in example 1.

After powder milling, micro-tablets were formed by using a semiautomatic fixture using approx. 3 lbs. of force for compression and a holding compression time of approx. 3 sec. The intact HUMIRA recovered in before-milling powder, after-milling powder and micro-tablets were tested using an HUMIRA immunoassay (Alpha Diagnostics Inc.). As in example 1), the before-milling powder recovery is the starting point of the micro-tableting process and the percentage of HUMIRA recovered using this manufacturing method was calculated using the before-milling powder recovery as 100%. The micro-tablet data and HUMIRA recovery values are detailed in Table 3.

The average density ranged from about 0.88 up to about 1.05 mg/mm$^3$ and the amount of bioactive HUMIRA recovered in the micro-tablets ranged from about 67 to about 80% to that prior to formation of the micro-tablet.

Once the powder was fully dry, it was then transferred to a low-bind round-bottom 2 ml tube. The milling process used a single Yttrium-stabilized zirconium ball having a mass of 0.445 g for a duration of 1.5 hours. The rotation method and temperature conditions were the same as used in Example 1.

After milling, micro-tablets were fabricated using an automatic fixture using 26 psi air pressure for compression, resulting in a compression force of about 1.8 lbs, and using a holding compression time of 3 sec. The air pressure for ejection was set at 28 psi (~1.82 lbs ejection force). The Biotin-Human Insulin micro-tablets were tested using an Insulin-biotin ELISA immunoassay kit (Alpha Diagnostics Inc., Cat#0030-20-1). The micro-tablet data and Biotin-Human Insulin recovery values are listed in Table 4.

TABLE 3

Micro-tablet Data and Adalimumab recoveries in Adalimumab Micro-tablet
Formulation: 90% HUMRIA Preparation (Drug and Excipients) from HUMIRA Pen

| Batch | Adalimumab Amount (mg) | PEG added (mg) | Micro-tablet Length (mm) | Micro-tablet Weight (mg) | Micro-tablet Density (mg/mm$^3$) | Absolute Micro-tablet Adalimumab Recovery |
|---|---|---|---|---|---|---|
| 1 | 40 | 4.4 | 3.28 ± 0.16 (N = 19) | 1.33 ± 0.05 (N = 19) | 1.03 ± 0.02 (N = 19) | 79.3% ± 2.3% (N = 6) |
| 2 | 40 | 4.4 | 4.12 ± 0.17 (N = 13) | 1.56 ± 0.08 (N = 13) | 0.96 ± 0.03 (N = 13) | 74% (N = 2) |
| 3 | 40 | 4.4 | 3.15 ± 0.03 (N = 23) | 1.22 ± 0.02 (N = 23) | 0.98 ± 0.01 (N = 23) | 66.7% (N = 2) |
| 4 | 48 | 5.3 | 3.25 ± 0.10 (N = 23) | 1.13 ± 0.04 (N = 23) | 0.88 ± 0.02 (N = 23) | 76.2% ± 2% (N = 9) |

Example 4: Micro-Tablets Comprising Insulin-Biotin Complex

Materials.

Biotin-Human Insulin solution (Alpha Diagnostics, cat# INSL16-BTN-B) and Poly Ethylene Glycol 3350 (PEG, Spectrum, Cat # P0125-500G).

Methods.

Biotinylated insulin (that insulin with an attached biotin molecule) was purchased from Alpha Diagnostics and received in a liquid form containing 2 mg/ml Insulin in 1×PBS (12 mM KPO4, 2.7 mM KCl, and 137 mM NaCl, pH). Ovalbumin was added to the solution at 1% by supplier. The solution purchased was placed in a low-bind 1.5 ml tube where PEG 3350 was added and mixed into the solution. The constituency of the final formulation for bathes 4-7 was the following: 8.7% biotin-human insulin complex, 5% PEG 3350, 43.5% Ovalbumin and 42.7% salts from 1×PBS during dialysis. Note batches, 1-3, were not included here due to large difference in the excipients amounts from batches 4-5. The solution was evaporated following the same conditions as the ones described in example 1.

TABLE 4

Micro-tablet Data and Biotin-Human Insulin Complex Recovery Data

| | Formulation | | | |
|---|---|---|---|---|
| Batch | 8.7% Biotin-Human Insulin Complex Micro-tablet Length (mm) | 5% peg 3350 Micro-tablet Weight (mg) | 43.5% Ovalbumin Micro-tablet Density (mg/mm$^3$) | 42.7% Salts from 1X PBS during dialysis Absolute Micro-tablet Insulin Recovery |
| 4 | 3.40 ± 0.07 (N = 4) | 1.35 ± 0.08 (N = 4) | 1.0 ± 0.05 (N = 4) | 94.2% ± 3.6% (N = 3) |
| 5 | 3.78 ± 0.04 (N = 5) | 1.35 ± 0.02 (N = 5) | 0.90 ± 0.01 (N = 5) | 69.9% ± 2.3% (N = 3) |

Example 5: Micro-Tablets Comprising Insulin

Materials.

Human Insulin (Imgenex, cat# IMR-232-250), Poly Ethylene Glycol 3350 (PEG, Spectrum, Cat # P0125-500G), Mannitol (Amresco, Cat#0122-500G), Povidone (ISP-Technologies, Plasdone C-30) and sterile water (APP Pharmaceutical, Cat#918510).

Methods.

Human insulin was mixed in solution with different excipients producing various batches for analysis. The formulation of each batch is detailed in Table 5. Batches 1-A, 2, 3B and 6B were not included due to different fabrication parameters. The excipients included PEG 3350 (lubricant), Mannitol (bulking agent) and Povidone (binder). These excipients and the API (human insulin) were dissolved in sterile water. The solution was evaporated using the same conditions as the ones described in example 1.

The milling process and parameters were the same as in example 4, using a low-bind round-bottom 2 ml tube and a single Yttrium-stabilized zirconium ball (mass of approx. 0.45 g) for a duration of 1.5 hours. The rotation method and temperature conditions were kept as used in Example 1.

After milling, micro-tablets were fabricated using an automatic fixture with 74.5 psi air pressure used for compression (resulting in a compression force of about 2.6 lbs) and a holding compression time of 3 sec. The air pressure for ejection was set at 80 psi (~2.7 lbs ejection force) The human Insulin micro-tablets were tested using Human Insulin ELISA immunoassay kit (Alpha Diagnostics Inc., Cat#0030N). The micro-tablet data and Human Insulin recovery values are detailed in Table 6.

TABLE 5

Formulation for Human Insulin Micro-tablets (weight %) *

| Batch | Human Insulin | PEG 3350 | Mannitol | Povidone |
|---|---|---|---|---|
| 1B | 25.8% | 5% | 69.2% | — |
| 3A | 23% | 5% | 72% | — |
| 4 | 89% | 5% | 6% | — |
| 5 | 89% | 5% | 4% | 2% |
| 6A | 80% | 5% | 13% | 2% |
| 7 | 80% | 5% | 13% | 2% |

* Note, the formulations are listed for Insulin batches 1b-7 because the composition in these batches changed from batch to batch, they did not do so for other batches.

TABLE 6

Micro-tablet Data and Human Insulin Recovery Data

| Batch | Micro-tablet Length (mm) | Micro-tablet Weight (mg) | Micro-tablet Density (mg/mm$^3$) | Absolute Micro-tablet Insulin Recovery |
|---|---|---|---|---|
| 1B | 2.10 ± 0.03 (N = 22) | 0.90 ± 0.01 (N = 22) | 1.08 ± 0.01 (N = 22) | 87.5% ± 0.8% (N = 5) |
| 3A | 2.32 ± 0.07 (N = 6) | 0.93 ± 0.02 (N = 6) | 1.01 ± 0.01 (N = 6) | 96.6% ± 2.6% (N = 3) |
| 4 | 2.42 ± 0.11 (N = 5) | 0.97 ± 0.04 (N = 5) | 1.01 ± 0.01 (N = 5) | 81.1% ± 3.1% (N = 3) |
| 5 | 2.42 ± 0.07 (N = 9) | 0.95 ± 0.02 (N = 9) | 0.99 ± 0.02 (N = 9) | 97.6% ± 1.6% (N = 6) |
| 6A | 1.95 ± 0.03 (N = 15) | 0.86 ± 0.01 (N = 15) | 1.12 ± 0.01 (N = 15) | 94.8% ± 3.5% (N = 3) |
| 7 | 2.09 ± 0.02 (N = 82) | 0.91 ± 0.01 (N = 82) | 1.09 ± 0.01 (N = 82) | 99.5% ± 0.3% (N = 16) |

CONCLUSION

The foregoing description of various embodiments of the invention has been presented for purposes of illustration and description. It is not intended to limit the invention to the precise forms disclosed. Many modifications, variations and refinements will be apparent to practitioners skilled in the art. For example, embodiments of the shaped masses described herein may contain and be used to deliver any number of drugs not necessarily described herein including for example anti-biotics, anti-viral compounds, various chemo-therapeutic agents, nutritional supplements, clotting factors, anti-parasitic agents, birth-control agents, fertility agents, anti-seizure compounds, vaccines and the like. The shaped masses may also be adapted in one or more of shape, dosage and consistency for various pediatric and neonatal applications, as well as various veterinary applications in a variety of mammals including, without limitation, use for delivery of drugs in bovine, canines, equine, feline, ovine and porcine applications.

Elements, characteristics, or acts from one embodiment can be readily recombined or substituted with one or more elements, characteristics or acts from other embodiments to form numerous additional embodiments within the scope of the invention. Moreover, elements that are shown or described as being combined with other elements, can, in various embodiments, exist as stand-alone elements. Further various embodiments expressly contemplate the negative recitation of any element that is shown or described in one or more embodiments. Hence, the scope of the present invention is not limited to the specifics of the described embodiments, but is instead limited solely by the appended claims.

What is claimed is:

1. A shaped mass comprising a drug portion and a layer of drug sequestering water swellable (DSWS) polymer, the drug portion comprising a drug having a biological activity in the body of a mammal which is degraded in the presence of secretions of the GI tract, the shaped mass configured to release the drug into wall tissue of the GI tract when the shaped mass is positioned in or adjacent said tissue such that the biological activity of the drug is substantially preserved from degradation by said GI tract secretions and wherein the DSWS polymer interacts with fluids in the wall tissue of the GI tract to expand into an in situ barrier structure surrounding the drug portion to control the release of the drug from the drug portion of the shaped mass into said tissue.

2. The shaped mass of claim 1, wherein the wall tissue is the wall tissue of a small intestine and the secretions comprise proteases and other proteolytic enzyme secretions of the small intestine.

3. The shaped mass of claim 1, wherein the shaped mass is formed by compression of a precursor material comprising the drug.

4. The shaped mass of claim 3, wherein an amount of biologically active drug in the shaped mass is at least about 80% by weight to that in the precursor material.

5. The shaped mass of claim 3, wherein the shaped mass is formed by compression of at least one of a powder or slurry comprising the drug.

6. The shaped mass of claim 3, wherein the precursor material has a particle size in the range of 50 to 450 µm.

7. The shaped mass of claim 1, wherein the drug comprises a protein or polypeptide.

8. The shaped mass of claim 1, wherein the DSWS swells in the presence of GI tract wall tissue fluid to form the in situ barrier structure.

9. The shaped mass of claim 8, wherein the DSWS polymer comprises a hydrogel.

10. The shaped mass of claim 1, wherein a ratio of DSWS polymer to drug in the shaped mass is selected to control a release rate of the drug.

11. The shaped mass of claim 1, wherein a ratio of DSWS polymer to drug is in a range of about 1:2 to 2:1.

12. The shaped mass of claim 1, wherein the DSWS polymer binds the drug by non-covalent interactions.

13. The shaped mass of claim 12, wherein the non-covalent interactions comprise hydrophobic interactions.

14. The shaped mass of claim 12, wherein the DSWS polymer comprises a cyclodextrin.

15. The shaped mass of claim 14, wherein the cyclodextrin comprises a β-cyclodextrin.

16. The shaped mass of claim 1, wherein the barrier structure slows a release rate of the drug in the intestinal wall tissue by a selective amount relative to when the barrier structure is not present.

17. The shaped mass of claim 16, wherein the reduction of the release rate of the drug is in a range of about 50 to 250%.

18. The shaped mass of claim 17, wherein the reduction of the release rate of the drug is in a range of about 50 to 150%.

19. The shaped mass of claim 1, wherein the shaped mass has a density in a range of about 0.8 to about 1.10 mg/mm$^3$.

20. The shaped mass of claim 1, wherein the drug comprises an immunoglobulin.

21. The shaped mass of claim 20, wherein the immunoglobulin comprises a TNF-α inhibiting antibody (TNFIA).

22. The shaped mass of claim 21, wherein the TNFIA comprises adalimumab.

23. The shaped mass of claim 22, wherein the shaped mass comprises about 20 to 60 mgrams of adalimumab.

24. The shaped mass of claim 21, wherein the TNFIA comprises infliximab.

25. The shaped mass of claim 21, wherein the TNFIA comprises etanercept.

26. The shaped mass of claim 20, wherein the immunoglobulin comprises an interleukin neutralizing antibody (INA).

27. The shaped mass of claim 26, wherein the interleukin to be neutralized comprises an interleukin from the interleukin-17 family of interleukins.

28. The shaped mass of claim 26, wherein the INA comprises secukinumab.

29. The shaped mass of claim 28, wherein the INA comprises a therapeutically effective dose of secukinumab for the treatment of plaque psoriasis.

30. The shaped mass of claim 29, wherein a dose of secukinumab in the shaped mass comprises about 3 to 10 mg of secukinumab.

31. The shaped mass of claim 26, wherein the INA comprises broadalumab.

32. The shaped mass of claim 31, wherein the INA comprises a therapeutically effective dose of broadalumab for the treatment of psoriatic arthritis.

33. The shaped mass of claim 32, wherein a dose of broadalumab in the shaped mass comprises about 10 to 20 mg of broadalumab.

34. The shaped mass of claim 26, wherein the INA comprises ixekizumab.

35. The shaped mass of claim 34, wherein the INA comprises a therapeutically effective dose of ixekizumab for the treatment of psoriatic Arthritis.

36. The shaped mass of claim 35, wherein a dose of ixekizumab in the shaped mass comprises about 2 to 6 mg of ixekizumab.

37. The shaped mass of claim 1, wherein the drug comprises a therapeutically effective dose of insulin for treatment of diabetes or other glucose regulation disorder.

38. The shaped mass of claim 37, wherein the shaped mass comprises between about 0.2 to about 0.8 mgrams of insulin.

39. The shaped mass of claim 1, wherein the drug comprises a therapeutically effective dose of an incretin for treatment of diabetes or other glucose regulation disorder.

40. The shaped mass of claim 39, wherein the incretin comprises exenatide.

41. The shaped mass of claim 40, wherein the shaped mass comprises between about 1 to about 5 mgms of exenatide.

42. The shaped mass of claim 1, wherein the shaped mass has a pellet shape or a tablet shape.

43. The shaped mass of claim 1, wherein the shaped mass has a tissue penetrating shape.

44. The shaped mass of claim 1, wherein the shaped mass comprises a pharmaceutical excipient.

45. The shaped mass of claim 44, wherein the pharmaceutical excipient comprises at least one of a lubricant, a binding agent or a bulking agent.

46. The shaped mass of claim 1, wherein the shaped mass has a first rate of release for the drug with the barrier structure and a faster second rate of release for the drug as the barrier structure degrades.

47. The shaped mass of claim 1, wherein the DSWS polymer interacts with the fluids in the wall tissue of the GI tract to swell and function as an anchor to fix the shaped mass in or adjacent said tissue.

48. The shaped mass of claim 47, wherein, to serve as an anchor, the shaped mass is increases in volume at least 3 times when the DSWS polymer interacts with the fluids in the wall of the GI tract.

49. The shaped mass of claim 47, wherein, to serve as an anchor, the shaped mass is increases in volume between 3 to 50 times when the DSWS polymer interacts with the fluids in the wall of the GI tract.

50. A shaped mass comprising a therapeutic agent and a drug sequestering water swellable (DSWS) polymer, the therapeutic agent having a biological activity in the body of a mammal which is degraded in the presence of secretions of the GI tract, the shaped mass configured to release the therapeutic agent into tissue of a selected tissue site when the shaped mass is positioned in or adjacent said tissue site such that the biological activity of the therapeutic agent is preserved, and wherein the DSWS polymer non-covalently interacts with the therapeutic agent in the presence of fluids in the tissue at the tissue site so as to decrease a release rate of therapeutic agent into the tissue at the tissue site as compared to a release rate of the therapeutic agent without the DSWS polymer present, wherein the DSWS polymer interacts with the fluids in the wall tissue of the GI tract to swell and function as an anchor to fix the shaped mass in or adjacent said tissue.

51. A shaped mass comprising a drug and a drug sequestering water swellable (DSWS) polymer, the drug having a biological activity in the body of a mammal which is degraded in the presence of secretions of the GI tract, the shaped mass configured to release the drug into wall tissue of the GI tract when the shaped mass is positioned in or adjacent said tissue such that the biological activity of the drug is substantially preserved and wherein the DSWS polymer non-covalently interacts with the drug in the presence of fluids in the wall tissue of the GI tract so as to decrease a release rate of drug into said tissue as compared to a release rate of the drug without the DSWS polymer present.

52. A shaped mass comprising an immunoglobulin and a drug sequestering water swellable (DSWS) polymer, the immunoglobulin having a binding affinity for an antigen in the body of a mammal which is degraded in the presence of secretions of the GI tract, the shaped mass configured to release the immunoglobulin into wall tissue of the GI tract when the shaped mass is positioned in or adjacent said tissue such that the binding affinity of the immunoglobulin is substantially preserved and wherein the DSWS polymer non-covalently interacts with the immunoglobulin in the presence of fluids in the wall tissue of the GI tract so as to decrease a release rate of immunoglobulin into said tissue as compared to a release rate of the immunoglobulin without the DSWS polymer present.

* * * * *